US006773907B2

(12) United States Patent
Hansen et al.

(10) Patent No.: US 6,773,907 B2
(45) Date of Patent: *Aug. 10, 2004

(54) SUBTILASE ENZYMES

(76) Inventors: Peter Kamp Hansen, Store Stensager 22, DK-4320 Lejre (DK); Peter Bauditz, Reersogade 18, 4 th., DK-2100 Copenhagen O (DK); Frank Mikkelsen, Bykildevej 5 st.tv., DK-2500 Valby (DK); Kim Vilbour Andersen, Tasingegade 31 4.th., DK-2100 Copenhagen O (DK); Carsten Andersen, Hoejeloft Vaenge 162, DK-3500 Vaerlose (DK); Mads Norregaard-Madsen, Munkerisvej 31 2tv, DK-5230 Odense M (DK)

( * ) Notice: Subject to any disclaimer, the term of this patent is extended or adjusted under 35 U.S.C. 154(b) by 0 days.

This patent is subject to a terminal disclaimer.

(21) Appl. No.: 10/242,549

(22) Filed: Sep. 12, 2002

(65) Prior Publication Data

US 2003/0171235 A1 Sep. 11, 2003

Related U.S. Application Data

(63) Continuation-in-part of application No. 09/573,301, filed on May 18, 2000, now abandoned, and a continuation-in-part of application No. 09/468,487, filed on Dec. 20, 1999, now abandoned, and a continuation-in-part of application No. 09/468,266, filed on Dec. 20, 1999, now abandoned, and a continuation-in-part of application No. 09/468,267, filed on Dec. 20, 1999, now abandoned, and a continuation-in-part of application No. 09/468,486, filed on Dec. 20, 1999, now abandoned, and a continuation-in-part of application No. 09/468,488, filed on Dec. 20, 1999, now abandoned, and a continuation-in-part of application No. 09/466,385, filed on Dec. 20, 1999, now abandoned, and a continuation-in-part of application No. 09/466,943, filed on Dec. 20, 1999, now abandoned, and a continuation-in-part of application No. 09/468,262, filed on Dec. 20, 1999, now abandoned, and a continuation-in-part of application No. 09/196,281, filed on Nov. 19, 1998, now Pat. No. 6,605,458, said application No. 09/468,487, is a continuation-in-part of application No. 09/344,517, filed on Jun. 25, 1999, now abandoned, which is a continuation-in-part of application No. 09/229,720, filed on Jan. 13, 1999, now abandoned, said application No. 09/468,266, is a continuation-in-part of application No. 09/299,868, filed on Jan. 13, 1999, now abandoned, said application No. 09/468,267, is a continuation-in-part of application No. 09/229,910, filed on Jan. 13, 1999, now abandoned, said application No. 09/468,486, is a continuation-in-part of application No. 09/229,719, filed on Jan. 13, 1999, now abandoned, said application No. 09/468,488, is a continuation-in-part of application No. 09/229,725, filed on Jan. 13, 1999, now abandoned, said application No. 09/466,385, is a continuation-in-part of application No. 09/229,188, filed on Jan. 13, 1999, now abandoned, said application No. 09/466,943, is a continuation-in-part of application No. 09/229,186, filed on Jan. 13, 1999, now abandoned, said application No. 09/468,262, is a continuation-in-part of application No. 09/229,906, filed on Jan. 13, 1999, now abandoned, said application No. 09/573,301, is a continuation-in-part of application No. 09/351,812, filed on Jul. 12, 1999, now abandoned.

(30) Foreign Application Priority Data

| | | |
|---|---|---|
| Nov. 21, 1997 | (DK) | 1332/97 |
| Dec. 18, 1998 | (DK) | 1998 01677 |
| Dec. 18, 1998 | (DK) | 1998 01670 |
| Dec. 18, 1998 | (DK) | 1998 01671 |
| Dec. 18, 1998 | (DK) | 1998 01675 |
| Dec. 18, 1998 | (DK) | 1998 01674 |
| Dec. 18, 1998 | (DK) | 1998 01673 |
| Dec. 18, 1998 | (DK) | 1998 01672 |
| Dec. 18, 1998 | (DK) | 1999 00706 |
| May 20, 1999 | (DK) | 1998 01676 |
| May 20, 1999 | (DK) | 1999 00701 |

(51) Int. Cl.[7] ................. C12N 9/54; C12N 15/57; C12N 15/75; C11D 3/386
(52) U.S. Cl. .............. 435/220; 435/69.1; 435/221; 435/222; 435/252.3; 435/320.1; 435/471; 510/350; 536/23.2
(58) Field of Search ................ 435/220, 69.1, 435/221, 252.3, 320.1, 471; 510/300, 350; 536/23.2

(56) References Cited

U.S. PATENT DOCUMENTS

RE34,606 E    5/1994  Estell et al. ............... 435/222

| | | | |
|---|---|---|---|
| 5,543,302 A | 8/1996 | Boguslawski et al. | 435/69.1 |
| 6,190,900 B1 * | 2/2001 | Sierkstra et al. | 435/221 |
| 6,558,938 B1 * | 5/2003 | Hansen et al. | 435/221 |
| 6,605,458 B1 * | 8/2003 | Hansen et al. | 435/220 |

FOREIGN PATENT DOCUMENTS

| | | |
|---|---|---|
| EP | 0 130 756 A1 | 1/1985 |
| EP | 0 214 435 A2 | 3/1987 |
| EP | 0 251 446 A2 | 1/1988 |
| EP | 0 260 105 B1 | 3/1988 |
| EP | 0 405 901 | 1/1991 |
| EP | 0 525 610 A2 | 2/1993 |
| WO | WO 87/04461 | 7/1987 |
| WO | WO 87/05050 | 8/1987 |
| WO | WO 88/08028 | 10/1988 |
| WO | WO 88/08033 | 10/1988 |
| WO | WO 89/06279 | 7/1989 |
| WO | WO 91/00345 | 1/1991 |
| WO | WO 94/02618 | 2/1994 |
| WO | WO 95/27049 | 10/1995 |
| WO | WO 95/29979 | 11/1995 |
| WO | WO 95/30010 | 11/1995 |
| WO | WO 95/30011 | 11/1995 |
| WO | WO 96/28566 | 9/1996 |
| WO | WO 96/34935 | 11/1996 |

OTHER PUBLICATIONS

Meloun, B., et al., 1985, "Complete primary structure of thermitase from *Thermoactinomyces vulgaris* and its structural features related to the subtilisin–type proteinases", FEBS Letters, vol. 183, pp. 195–200.*

Koide, Y., et al., 1986, "Cloning and sequencing of the major intracellular serine protease gene of *Bacillus subtilis*", Journal of Bacteriology, vol. 167, pp. 110–116.*

Tatsumi, H., et al., 1989, "A full length cDNA clone for the alkaline protease of *Aspergillus oryzae*: Structural analysis and expression in *Saccharomyces cerevisiae*", Molecular and General Genetics, vol. 1219, pp. 33–38.*

Takekawa, S., et al., 1990, "Proteases involved in generation of [beta]– and [alpha]–amylases from a large amylase precursor in *Bacillus polymyxa*", Journal of Bacteriology, vol. 173, pp. 6820–6825.*

Siezen, R.J., et al., 1991, "Homology modeling and protein engineering strategy of subtilases, the family of subtilisin–like serine proteinases", Protein Engineering, vol. 4, pp. 719–737.*

Kato et al., 1992, PIR database Accession No. S27501.*

Schnell, N., et al., 1992, "Analysis of genes involved in the biosynthesis of lantobiotic epidermin", European Journal of Biochemistry, vol. 204, pp. 57–68.*

Whitby, P.W., et al., 1992, "The cloning and nucleotide sequence of the serine protease gene (aspA) of *Aeromonas salmonicida* ssp. salmonicida", FEMS Microbiology Letters, vol. 78, pp. 65–71.*

Geremia, R. A., et al., 1993, "Molecular characterization of the proteinase–encoding gene, prb 1, related to mycoparasitism by *Trichoderma haraianum*", Molecular Microbiology, vol. 8, pp. 603–613.*

MacIver, B., et al., 1994, "Cloning and sequencing of a serine protease gene from a thermophilic Bacilus species and its expression in *E. coli*", Applied and Environmental Microbiology, vol. 60, pp. 3981–3988.*

Abraham, L.D., et al., 1995, "Factors affecting autolysis of a subtilisin–like serine proteinase secreted by *Ophiosotoma picae* and identification of the cleavage site", Biochimica et Biophysica Acta, vol. 1245, pp. 76–84.*

Piret et al., 1995, SPTREMBL database Accession No. Q53863.*

Kwon, Y.T., et al., 1995, "Cloning and characterization of the gene encoding an extracellular alkaline serine protease from *Vibrio metschnikovii* strain RH530", vol. 152, pp. 59–63.*

Gilbert, C., et al., 1996, "A new cell surface proteinase: Sequencing and analysis of the prtB gene from *Lactobacillus delbrueckii* subsp. bulgaricus", Journal of Bacteriology, vol. 178, pp. 3059–3065.*

Redenbach, M., et al., 1996, "A set of ordered cosmids and a detailed genetic and physical map for the 8 Mb *Streptomyces coelicolor* A3(2) chromosome", Molecular Microbiology, vol. 21, pp. 77–96/.*

Siezen, R.J., et al., 1997, "Subtilases: The superfamily of subtilisin–like proteases", Protein Science, vol. 6, pp. 501–523.*

Sloma et al., May 1997, SPTREMBL database Accession No. P97097.*

Russel et al. ( 1987) J. Mol. Biol. 193: 803–813.

Thomas et al. ( 1985) Nature 318( 28): 375–376.

Russel et al. (1987) Nature 328( 6): 496–500.

Graycar et al., ( 1992) Annals New York Acad. of Sciences 672: 71–79.

* cited by examiner

*Primary Examiner*—Nashaat T. Nashed
*Assistant Examiner*—William W. Moore
(74) *Attorney, Agent, or Firm*—Elias J. Lambiris

(57) ABSTRACT

The present invention relates to subtilase enzymes of the I-S1 and I-S2 sub-groups having an additional amino acid in the active site loop (b) region from positions 95 to 103. The variant subtilases of the present invention exhibit improved wash performance in a detergent in comparison to its parent enzyme.

226 Claims, 5 Drawing Sheets

Figure 1A

```
No:    1         10        20        30        40        50
a)     AQSVPYGVSQIKAPALHSQGYTGSNVKVAVIDSGIDSSHPDLKVAGGASM
b)     AQSVPWGISRVQAPAAHNRGLTGSGVKVAVLDTGI*STHPDLNIRGGASF

No:              60        70        80        90        100
a)     VPSETNPFQDNNSHGTHVAGTVAALNNSIGVLGVAPSASLYAVKVLGADG
b)     VPGEPST*QDGNGHGTHVAGTIAALNNSIGVLGVAPSAELYAVKVLGASG

No:              110       120       130       140       150
a)     SGQYSWIINGIEWAIANNMDVINMSLGGPSGSAALKAAVDKAVASGVVVV
b)     SGSVSSIAQGLEWAGNNGMHVANLSLGSPSPSATLEQAVNSATSRGVLVV

No:              160       170       180       190       200
a)     AAAGNEGTSGSSSTVGYPGKYPSVIAVGAVDSSNQRASFSSVGPELDVMA
b)     AASGNSG*AGS***ISYPARYANAMAVGATDQNNNRASFSQYGAGLDIVA

No:              210       220       230       240       250
a)     PGVSIQSTLPGNKYGAYNGTSMASPHVAGAAALILSKHPNWTNTQVRSSL
b)     PGVNVQSTYPGSTYASLNGTSMATPHVAGAAALVKQKNPSWSNVQIRNHL

No:              260       270  275
a)     ENTTTKLGDSFYYGKGLINVQAAAQ
b)     KNTATSLGSTNLYGSGLVNAEAATR
```

| No.: | 10 | 20 | 30 | 40 | 50 | a) AQSVPYGVSQIKAPALHSQGYTGSNVKVAVIDSGIDSSHPDLKVAGGASM
g) AQTVPYGIPLIKADKVQAQGFKGANVKVAVLDTGIQASHPDLNVVGGASF

| No.: | 60 | 70 | 80 | 90 | 100 | a) VPSETNPFQDNNSHGTHVAGTVAALNNSIGVLGVAPSASLYAVKVLGADG
g) VAGEAYN*TDGNGHGTHVAGTVAALDNTTGVLGVAPSVSLYAVKVLNSSG

| No.: | 110 | 120 | 130 | 140 | 150 | a) SGQYSWIINGIEWAIANNMDVINMSLGGPSGSAALKAAVDKAVASGVVVV
b) SGTYSGIVSGIEWATTNGMDVINMSLGGPSGSTAMKQAVDNAYARGVVVV

| No.: | 160 | 170 | 180 | 190 | 200 | a) AAAGNEGTSGSSSTVGYPGKYPSVIAVGAVDSSNQRASFSSVGPELDVMA
b) AAAGNSGSSGNTNTIGYPAKYDSVIAVGAVDSNSNRASFSSVGAELEVMA

| No.: | 210 | 220 | 230 | 240 | 250 | a) PGVSIQSTLPGNKYGAYNGTSMASPHVAGAAALILSKHPNWTNTQVRSSL
b) PGAGVYSTYPTSTYATLNGTSMASPHVAGAAALILSKHPNLSASQVRNRL

| No.: | 260 | 270 | 275 | a) ENTTTKLGDSFYYGKGLINVQAAAQ
b) SSTATYLGSSFYYGKGLINVEAAAQ

SUBTILASE ENZYMES

CROSS-REFERENCE TO RELATED APPLICATIONS

This application is a continuation-in-part of U.S. application Ser. No. 09/196,281, now U.S. Pat. No. 6,605,458, U.S. application Ser. Nos. 09/468,487 abandoned, 09/468,266 abandoned, 09/468,267 abandoned, 09/468,486 abandoned, 09/468,488 abandoned, 09/466,385 abandoned, 09/466,943 abandoned, 09/468,262 abandoned, and 09/573,301 abandoned, filed Nov. 19, 1998, Dec. 20, 1999, Dec. 20, 1999, Dec. 20, 1999, Dec. 20, 1999, Dec. 20, 1999, Dec. 20, 1999, Dec. 20, 1999, Dec. 20, 1999, and May 18, 2000, respectively, and claims, under 35 U.S.C. 119, priority of Danish application nos. 1332/97, PA 1998 01677, PA 1999 00706, PA 1998 01676, PA 1998 01675, PA 1998 01674, PA 1998 01673, PA 1998 01672, PA 1998 01671, PA 1998 01670, and PA 1999 00701, filed Nov. 21, 1997, Dec. 18, 1998, May 20, 1999, Dec. 18, 1998, Dec. 18, 1998, Dec. 18, 1998, Dec. 18, 1998, Dec. 18, 1998, Dec. 18, 1998, Dec. 18, 1998, and May 20, 1999, respectively. Application Ser. No. 09/468,487 is a continuation-in-part of application Ser. No. 09/344,517 filed Jun. 25, 1999 abandoned, which is a continuation-in-part of application Ser. No. 09/229,720 filed Jan. 13, 1999 abandoned. Application Ser. No. 09/468,266 is a continuation-in-part of application Ser. No. 09/229,868 filed Jan. 13, 1999 abandoned. Application Ser. No. 09/468,267 is a continuation-in-part of application Ser. No. 09/229,910 filed Jan. 13, 1999 abandoned. Application Ser. No. 09/468,486 is a continuation-in-part of application Ser. No. 09/229,719 filed Jan. 13, 1999 abandoned. Application Ser. No. 09/468,488 is a continuation-in-part of application Ser. No. 09/229,725 filed Jan. 13, 1999 abandoned. Application Ser. No. 09/466,385 is a continuation-in-part of application Ser. No. 09/229,188 filed Jan. 13, 1999 abandoned. Application Ser. No. 09/466,943 is a continuation-in-part of application Ser. No. 09/229,186 filed Jan. 13, 1999 abandoned. Application Ser. No. 09/468,262 is a continuation-in-part of application Ser. No. 09/229,906 filed Jan. 13, 1999 abandoned. Application Ser. No. 09/573,301 is a continuation-in-part of application Ser. No. 09/351,812 filed Jul. 12, 1999 abandoned. The contents of all of the above applications is incorporated herein by reference.

BACKGROUND OF THE INVENTION

1. Field of the Invention

The present invention relates to subtilase enzymes having an additional amino acid in the active site loop (b) region from position 95 to 103 and detergent and cleaning compositions comprising same. The invention further relates to genes coding for the expression of said enzymes when inserted into a suitable host cell or organism; and host cells transformed therewith, and methods for producing the enzymes.

2. Description of the Related Art

In the detergent industry, enzymes have been used in washing formulations for more than 30 years. Such enzymes include proteases, lipases, amylases, cellulases, as well as other enzymes, or mixtures thereof. The most important commercially are proteases.

An increasing number of commercially used proteases are protein engineered variants of naturally occurring wild-type proteases, e.g. DURAZYM® (Novo Nordisk A/S), RELASE® (Novo Nordisk A/S), MAXAPEM® (Gist-Brocades N.V.), PURAFECT® (Genencor International, Inc.).

In addition, a number of protease variants have been described in the art, such as in EP 130756 (GENENTECH) (corresponding to U.S. Reissue Pat. No. 34,606 (GENENCOR)); EP 214435 (HENKEL); WO 87/04461 (AMGEN); WO 87/05050 (GENEX); EP 260105 (GENENCOR); Thomas, Russell, and Fersht, Nature, 318, 375–376 (1985); Thomas, Russell, and Fersht, J. Mol. Biol., 193, 803–813 (1987); Russel and Fersht, Nature, 328, 496–500 (1987); WO 88/08028 (Genex); WO 88/08033 (Amgen); WO 95/27049 (SOLVAY S.A.); WO 95/30011 (PROCTER & GAMBLE COMPANY); WO 95/30010 (PROCTER & GAMBLE COMPANY); WO 95/29979 (PROCTER & GAMBLE COMPANY); U.S. Pat. No. 5,543,302 (SOLVAY S.A.); EP 251 446 (GENENCOR); WO 89/06279 (NOVO NORDISK A/S); WO 91/00345 (NOVO NORDISK A/S); EP 525 610 A1 (SOLVAY); and WO 94/02618 (GIST-BROCADES N.V.).

However, even though a number of useful protease variants have been described, there is still a need for new improved proteases or protease variants for a number of industrial uses.

Therefore, an object of the present invention is to provide improved proteases or protein engineered protease variants, especially for use in the detergent industry.

SUMMARY OF THE INVENTION

The present inventors have found that subtilisins wherein at least one of the active site loops is longer than those presently known, exhibit improved wash performance properties in detergent compositions. The identification thereof was done by constructing subtilisin variants, especially of subtilisin 309 (BLSAVI or SAVINASE®), which exhibited improved wash performance properties in detergent compositions relative to the parent wild-type enzyme. This was described in our earlier application DK 1332/97, which published as WO 99/27082.

It has now been found that certain subtilases or variants thereof of the I-S1 (true "subtilisins") and I-S2 (high alkaline subtilisins) sub-groups having at least one additional amino acid residue in the active site loop (b) region from position 95 to 103, exhibit surprisingly improved wash performance in comparison to those presently known and those described in said application.

The improved proteases according to the invention may be obtained by isolation from natural resources or by the introduction of at least one further amino acid residue (an insertion) in the active site loop (b) region in a wild-type subtilase (for a definition of the active site loops and the numbering of positions see below).

Although this finding was done in subtilisin 309, it is predicted that it will be possible to produce or isolate similar advantageous subtilases or subtilase variants.

Furthermore it will be possible to specifically screen natural isolates to identify wild-type subtilases comprising an active site loop (b) region which is longer than the corresponding active site loop region in known wild-type subtilases, such as subtilisin 309, which subtilases can be considered to have an inserted amino acid residue in the active site loop (b) region, and exhibiting excellent wash performance in a detergent, in comparison to their closest related known subtilisin, such as subtilisin 309.

Concerning alignment and numbering reference is made to FIGS. 1A, 1B, 2A and 2B showing alignments between subtilisin BPN' (BASBPN) (a) and subtilisin 309 (BLSAVI) (b), and alignments between subtilisin BPN' (a) (BASBPN) and subtilisin Carlsberg (g) (BLSCAR). These alignments are used herein as a reference for numbering the residues.

The seven active site loops (a) to (g) are herein defined as the segments of amino acid residues provided below (including the terminal amino acid residues):

(a) the region between amino acid residue 33 and 43;
(b) the region between amino acid residue 95 and 103;
(c) the region between amino acid residue 125 and 132;
(d) the region between amino acid residue 153 and 173;
(e) the region between amino acid residue 181 and 195;
(f) the region between amino acid residue 202 and 204;
(g) the region between amino acid residue 218 and 219.

Accordingly, in a first aspect the invention relates to an isolated (i.e. greater than 10% pure) subtilase enzyme of the I-S1 and I-S2 sub-groups having at least one additional amino acid residue in the active site loop (b) region from position 95 to 103, whereby said additional amino acid residue(s) corresponds to the insertion of at least one amino acid residue.

In a second aspect the invention relates to an isolated DNA sequence encoding a subtilase variant of the invention.

In a third aspect the invention relates to an expression vector comprising an isolated DNA sequence encoding a subtilase variant of the invention.

In a fourth aspect the invention relates to a microbial host cell transformed with an expression vector according to the third aspect.

In a further aspect the invention relates to the production of the subtilisin enzymes of the invention.

The enzymes of the invention can generally be produced by either cultivation of a microbial strain from which the enzyme was isolated and recovering the enzyme in substantially pure form; or by inserting an expression vector according to the third aspect of the invention into a suitable microbial host, cultivating the host to express the desired subtilase enzyme, and recovering the enzyme product.

Further the invention relates to a composition comprising a subtilase or subtilase variant of the invention.

Even further the invention relates to the use of the enzymes of the invention for a number of industrial relevant uses, in particular for use in cleaning and detergent compositions, comprising the subtilisin enzymes of the present invention.

Definitions

Prior to discussing this invention in further detail, the following terms and conventions will first be defined.

NOMENCLATURE OF AMINO ACIDS

A = Ala = Alanine
V = Val = Valine
L = Leu = Leucine
I = Ile = Isoleucine
P = Pro = Proline
F = Phe = Phenylalanine
W = Trp = Tryptophan
M = Met = Methionine
G = Gly = Glycine
S = Ser = Serine
T = Thr = Threonine
C = Cys = Cysteine
Y = Tyr = Tyrosine
N = Asn = Asparagine
Q = Gln = Glutamine
D = Asp = Aspartic Acid
E = Glu = Glutamic Acid
K = Lys = Lysine
R = Arg = Arginine -continued H = His = Histidine
X = Xaa = Any amino acid

NOMENCLATURE OF NUCLEIC ACIDS

A = Adenine
G = Guanine
C = Cytosine
T = Thymine (only in DNA)
U = Uracil (only in RNA)

Nomenclature and Conventions for Designation of Variants

In describing the subtilases of the present invention, the following nomenclatures and conventions have been adapted for ease of reference:

A frame of reference is first defined by aligning the isolated or parent wild-type enzyme with subtilisin BPN' (BASBPN).

The alignment can be obtained by the GAP routine of the GCG package version 9.1 to number the variants using the following parameters: gap creation penalty=8 and gap extension penalty=8 and all other parameters kept at their default values.

Another method is to use known recognized alignments between subtilases, such as the alignment indicated in WO 91/00345. In most cases the differences will not be of any importance.

Such alignments between subtilisin BPN' (BASBPN) and subtilisin 309 (BLSAVI) and subtilisin Carlsberg (BLSCAR), respectively are indicated in FIGS. 1A, 1B, 2A, and 2B. They define a number of deletions and insertions in relation to BASBPN. In FIG. 1A, subtilisin 309 has 6 deletions in positions 36, 58, 158, 162, 163, and 164 in comparison to BASBPN, whereas in FIG. 1B subtilisin 309 has the same deletions in positions 36, 56, 159, 164, 165, and 166 in comparison to BASBPN. In FIG. 2A subtilisin Carlsberg has one deletion in position 58 in comparison to BASBPN, whereas in FIG. 2B subtilisin Carlsberg has the one deletion in position 56 in comparison to BASBPN. These deletions are indicated in FIGS. 1A, 1B, 2A, and 2B by asterisks (*).

The various modifications performed in a wild-type enzyme are indicated in general using three elements as follows:

Original Amino Acid Position Substituted Amino Acid

Thus, the notation G195E means a substitution of glycine in position 195 with glutamic acid.

In the case when the original amino acid residue may be any amino acid residue, a short hand notation may at times be used indicating only the position and substituted amino acid, Position Substituted Amino Acid Such a notation is particularly relevant in connection with modification(s) in homologous subtilases (vide infra).

Similarly when the identity of the substituting amino acid residue(s) is immaterial, the following short hand notation can be used:

Original Amino Acid Position

When both the original amino acid(s) and substituted amino acid(s) may comprise any amino acid, then only the position is indicated, e.g., 170.

When the original amino acid(s) and/or substituted amino acid(s) may comprise more than one, but not all amino acid(s), then the selected amino acids are indicated inside brackets { }, Original Amino Acid Position {Substituted Amino Acid$_I$, . . . , Substituted Amino Acid$_n$}

For specific variants the specific three or one letter codes are used, including the codes Xaa and X to indicate any amino acid residue.

Substitutions:

The substitution of glutamic acid for glycine in position 195 is designated as:

Gly195Glu or G195E or the substitution of any amino acid residue acid for glycine in position 195 is designated as:

Gly195Xaa or G195X or Gly195 or G195

The substitution of serine for any amino acid residue in position 170 would thus be designated Xaa170Ser or X170S or 170Ser or 170S.

Thus, 170Ser comprises e.g. both a Lys170Ser modification in BASBPN and an Arg170Ser modification in BLSAVI (cf. FIG. 1).

For a modification where the original amino acid(s) and/or substituted amino acid(s) may comprise more than one, but not all amino acid(s), the substitution of glycine, alanine, serine or threonine for arginine in position 170 would be indicated by Arg170{Gly,Ala,Ser,Thr} or R170{G,A,S,T} to indicate the variants

R170G, R170A, R170S, and R170T.

Deletions:

A deletion of glycine in position 195 is indicated by:

Gly195* or G195*

Similarly, the deletion of more than one amino acid residue, such as the deletion of glycine and leucine in positions 195 and 196 is designated Gly195*+Leu196* or G195*+L196*

Insertions:

The insertion of an additional amino acid residue such as e.g. a lysine after G195 is designated:

Gly195GlyLys or G195GK; or when more than one amino acid residue is inserted, such as e.g. a Lys, Ala and Ser after G195 this is shown as:

Gly195GlyLysAlaSer or G195GKAS (SEQ ID NO: 1)

In such cases the inserted amino acid residue(s) are numbered by the addition of lower case letters to the position number of the amino acid residue preceding the inserted amino acid residue(s). In the above example the sequences 194 to 196 would thus be:

```
           194 195 196                    (SEQ ID NO: 2)
BLSAVI     A - G - L 194 195 195a 195b 195c 196
Variant    A - G - K  - A  - S  - L
```

In cases where an amino acid residue identical to the existing amino acid residue is inserted it is clear that a degeneracy in the nomenclature arises. If for example a glycine is inserted after the glycine in the above example this would be indicated by G195GG. The same actual change could just as well be indicated as A194AG for the change from

```
           194 195 196                    (SEQ ID NO: 3)
BLSAVI     A - G - L
to 194 195  195a 196
Variant    A - G -  G  - L
           194 194a 195  196
```

Such instances will be apparent to the skilled person. Thus, it is to be understood that the indication G195GG and corresponding indications encompass such equivalent degenerate indications.

Sometimes it is desired to both perform a modification and an insertion at the same position. This situation is also covered by the present definitions. Thus, S130TP indicates that the serine in position 130 has been replaced by a tyrosine and a proline. Another way to describe this variant is S130SP+S130T.

Filling a Gap:

Where a deletion in an enzyme exists in the reference comparison with the subtilisin BPN' sequence used for the numbering, an insertion in such a position is indicated as:

*36Asp or *36D for the insertion of an aspartic acid at position 36.

Multiple Modifications

Variants comprising multiple modifications are separated by pluses, e.g.:

Arg170Tyr+Gly195Glu or R170Y+G195E representing modifications in positions 170 and 195 substituting tyrosine and glutamic acid for arginine and glycine, respectively, or e.g. Tyr167{Gly,Ala,Ser,Thr}+Arg170{Gly,Ala,Ser,Thr} designates the variants

| | |
|---|---|
| Tyr167Gly + Arg170Gly, | Tyr167Gly + Arg170Ala, |
| Tyr167Gly + Arg170Ser, | Tyr167Gly + Arg170Thr, |
| Tyr167Ala + Arg170Gly, | Tyr167Ala + Arg170Ala, |
| Tyr167Ala + Arg170Ser, | Tyr167Ala + Arg170Thr, |
| Tyr167Ser + Arg170Gly, | Tyr167Ser + Arg170Ala, |
| Tyr167Ser + Arg170Ser, | Tyr167Ser + Arg170Thr, |
| Tyr167Thr + Arg170Gly, | Tyr167Thr + Arg170Ala, |
| Tyr167Thr + Arg170Ser, and | Tyr167Thr + Arg170Thr. |

This nomenclature is particularly relevant for designating modifications that are substitutions, insertions or deletions of amino acid residues having specific common properties, such as residues of positive charge (K, R, H), negative charge (D, E), or conservative amino acid modification(s) of e.g. Tyr167{Gly,Ala,Ser,Thr}+Arg170{Gly,Ala,Ser,Thr}, which signifies substituting a small amino acid for another small amino acid. See section "Detailed description of the invention" for further details.

Numbering of Amino Acid Positions/Residues

For purposes of this invention, the numbering of amino acids corresponds to that of the amino acid sequence of subtilase BPN' (BASBPN). For further description of the amino acid sequence of subtilisin BPN', see FIGS. 1 and 2, or Siezen et al., *Protein Engng.*, 4, 719–737 (1991).

Proteases

Enzymes cleaving the amide linkages in protein substrates are classified as proteases, or (interchangeably) peptidases (see Walsh, 1979, *Enzymatic Reaction Mechanisms*. W. H. Freeman and Company, San Francisco, Chapter 3).

Serine Proteases

A serine protease is an enzyme which catalyzes the hydrolysis of peptide bonds, and in which there is an essential serine residue at the active site (White, Handler and Smith, *"Principles of Biochemistry,"* Fifth Edition, McGraw-Hill Book Company, NY, pp. 271–272 (1973)).

The bacterial serine proteases have molecular weights in the 20,000 to 45,000 Dalton range. They are inhibited by diisopropylfluorophosphate. They hydrolyze simple terminal esters and are similar in activity to eukaryotic chymotrypsin, also a serine protease. A more narrow term, alkaline protease, covering a sub-group, reflects the high pH optimum of some of the serine proteases, from pH 9.0 to 11.0 (for review, see Priest, *Bacteriological Rev.*, 41, 711–753 (1977)).

Subtilases

A sub-group of the serine proteases tentatively designated subtilases has been proposed by Siezen et al., *Protein Engng.*, 4, 719–737 (1991) and Siezen et al., *Protein Science*, 6, 501–523 (1997). They are defined by homology analysis of more than 170 amino acid sequences is of serine proteases previously referred to as subtilisin-like proteases. A subtilisin was previously often defined as a serine protease produced by gram-positive bacteria or fungi, and according to Siezen et al. now is a subgroup of the subtilases. A wide variety of subtilases have been identified, and the amino acid sequence of a number of subtilases has been determined. For a more detailed description of such subtilases and their amino acid sequences reference is made to Siezen et al. (1997).

One subgroup of the subtilases, I-S1 or "true#" subtilisins, comprises the "classical" subtilisins, such as subtilisin 168 (BSS168), subtilisin BPN', subtilisin Carlsberg (ALCALASE®, NOVO NORDISK A/S), and subtilisin DY (BSSDY).

A further subgroup of the subtilases, I-S2 or high alkaline subtilisins, is recognized by Siezen et al. Sub-group I-S2 proteases are described as highly alkaline subtilisins and comprises enzymes such as subtilisin PB92 (BAALKP) (MAXACAL®, Gist-Brocades NV), subtilisin 309 (SAVINASE®, NOVO NORDISK A/S), subtilisin 147 (BLS147) (ESPERASE®, NOVO NORDISK A/S), and alkaline elastase YaB (BSEYAB).

List of Acronyms for Subtilases:

I-S1

Subtilisin 168, BSS168 (BSSAS (Subtilisin amylosacchariticus)), BSAPRJ (Subtilisin J), BSAPRN (Subtilisin NAT), BMSAMP (Mesentericopeptidase), Subtilisin BPN', BASBPN, Subtilisin DY, BSSDY, Subtilisin Carlsberg, BLSCAR (BLKERA (Keratinase), BLSCA1, BLSCA2, BLSCA3), BSSPRC, Serine protease C BSSPRD, Serine protease D

I-S2

Subtilisin Sendai, BSAPRS

Subtilisin ALP 1, BSAPRQ,

Subtilisin 147, Esperase®, BLS147 (BSAPRM (SubtilisinAprM), BAH101)

Subtilisin 309, SAVINASE®, BLS309/BLSAVI (BSKSMK (M-protease), BAALKP (Subtilisin PB92, Bacillus alkalophilic alkaline protease), BLSUBL (Subtilisin BL)), Alkaline elastase YaB, BYSYAB

"SAVINASE®"

SAVINASE® is marketed by NOVO NORDISK A/S. It is subtilisin 309 from *B. lentus* and differs from BAALKP only in one position (N87S, see FIG. 1). SAVINASE® has the amino acid sequence designated b) in FIG. 1.

Parent Subtilase

The term "parent subtilase" describes a subtilase defined according to Siezen et al. (1991 and 1997). For further details see description of "SUBTILASES" immediately above. A parent subtilase may also be a subtilase isolated from a natural source, wherein subsequent modification have been made while retaining the characteristic of a subtilase. Alternatively the term "parent subtilase" may be termed "wild-type subtilase".

Modification(s) of a Subtilase Variant

The term "modification(s)" used herein is defined to include chemical modification of a subtilase as well as genetic manipulation of the DNA encoding a subtilase. The modification(s) can be replacement(s) of the amino acid side chain(s), substitution(s), deletion(s) and/or insertions in or at the amino acid(s) of interest.

Subtilase Variant

In the context of this invention, the term subtilase variant or mutated subtilase means a subtilase that has been produced by an organism which is expressing a mutant gene derived from a parent microorganism which possessed an original or parent gene and which produced a corresponding parent enzyme, the parent gene having been mutated in order to produce the mutant gene from which said mutated subtilase protease is produced when expressed in a suitable host.

Homologous Subtilase Sequences

The present invention relates to modified subtiliases comprising an insertion in the active site loop (b) region in the subtilase SAVINASE and other parent (wild-type) subtilases, which have a homologous primary structure to that of SAVINASE®. The homology between two amino acid sequences is in this context described by the parameter "identity".

In order to determine the degree of identity between two subtilases the GAP routine of the GCG package version 9.1 can be applied using the same settings as indicated above. The output from the routine is besides the amino acid alignment the calculation of the "Percent Identity" between the two sequences.

Based on this description it is routine for a person skilled in the art to identify suitable homologous subtilases and corresponding homologous active site loop regions, which can be modified according to the invention.

Wash Performance

The ability of an enzyme to catalyze the degradation of various naturally occurring substrates present on the objects to be cleaned during e.g. wash or hard surface cleaning is often referred to as its washing ability, wash-ability, detergency, or wash performance. Throughout this application the term wash performance will be used to encompass this property.

Isolated DNA Sequence

The term "isolated", when applied to a DNA sequence molecule, denotes that the DNA sequence has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, Nature, 316, 774–78 (1985)). The term "an isolated DNA sequence" may alternatively be termed "a cloned DNA sequence".

Isolated Protein

When applied to a protein, the term "isolated" indicates that the protein has been removed from its native environment.

In a preferred form, the isolated protein is substantially free of other proteins, particularly other homologous proteins (i.e. "homologous impurities" (see below)).

An isolated protein is greater than 10% pure, preferably greater than 20% pure, more preferably greater than 30% pure, as determined by SDS-PAGE. Further it is preferred to provide the protein in a highly purified form, i.e., greater than 40% pure, greater than 60% pure, greater than 80% pure, more preferably greater than 95% pure, and even more preferably greater than 99% pure, as determined by SDS-PAGE.

The term "isolated protein" may alternatively be termed "purified protein".

Homologous Impurities

The term "homologous impurities" means any impurity (e.g. a polypeptide other than the polypeptide of the invention) which originates from the homologous cell where the polypeptide of the invention is originally obtained from.

Obtained from

The term "obtained from" as used herein in connection with a specific microbial source, means that the polynucleotide and/or polypeptide is produced by the specific source, or by a cell in which a gene from the source has been inserted.

Substrate

The term "Substrate" used in connection with a substrate for a protease should be interpreted in its broadest form as comprising a compound containing at least one peptide bond susceptible to hydrolysis by a subtilisin protease.

Product

The term "product" used in connection with a product derived from a protease enzymatic reaction should in the context of this invention be interpreted to include the products of a hydrolysis reaction involving a subtilase protease. A product may be the substrate in a subsequent hydrolysis reaction.

BRIEF DESCRIPTION OF THE DRAWINGS

Figure 1B:
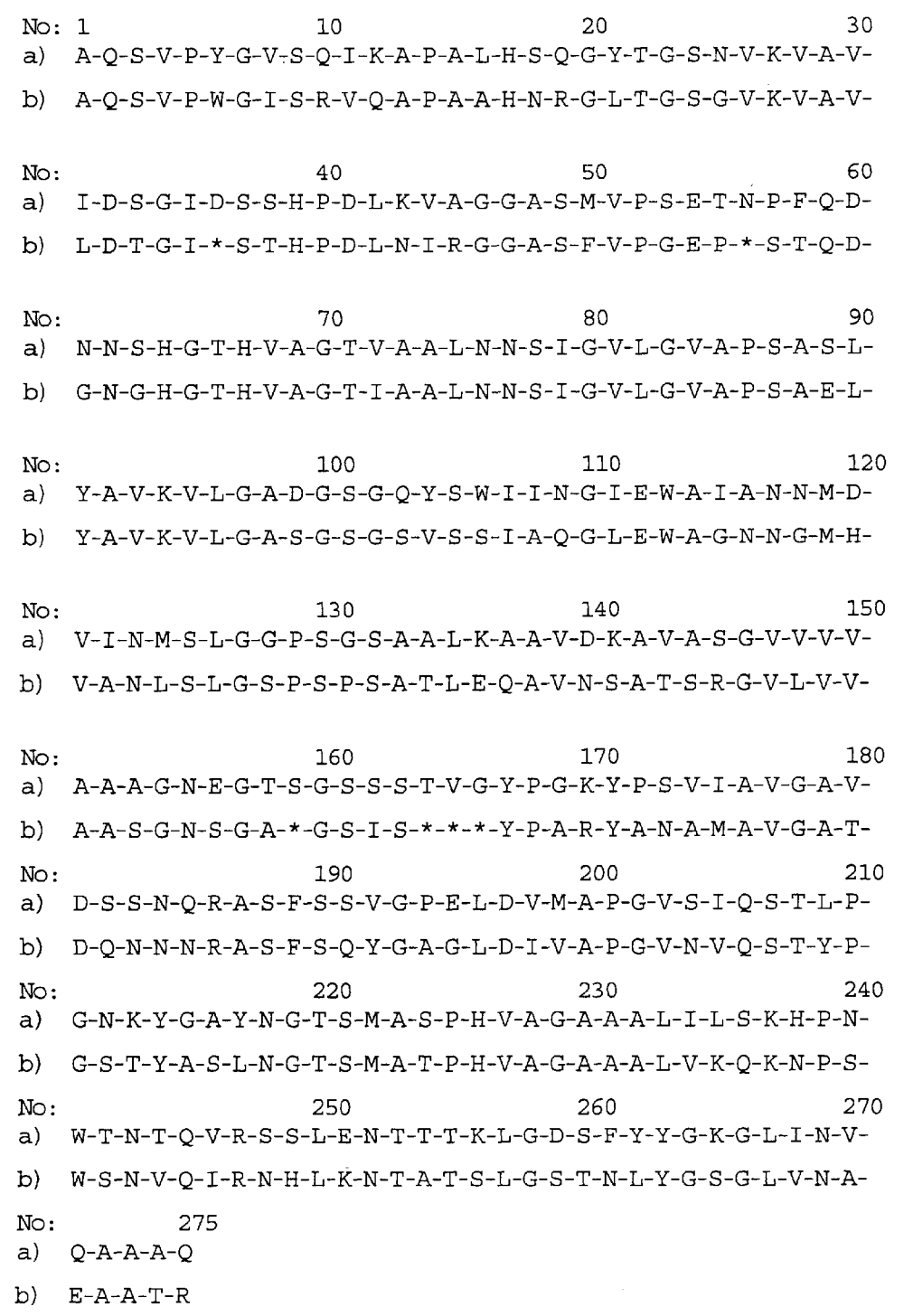

FIG. 1A shows an alignment of subtilisin BPN' (a) (SEQ ID NO: 4) and SAVINASE® (b) (SEQ ID NO: 5) using the GAP routine mentioned above.

FIG. 1B shows the alignment of subtilisin BPN' (SEQ ID NO: 4) and SAVINASE® (SEQ ID NO: 5) as taken from WO 91/00345.

FIG. 2A shows an alignment of subtilisin BPN' (SEQ ID NO: 4) and subtilisin Carlsberg (SEQ ID NO: 6) using the GAP routine mentioned above.

FIG. 2B shows the alignment of subtilisin BPN' (SEQ ID NO: 4) and subtilisin Carlsberg (SEQ ID NO: 6) as taken from WO 91/00345.

DETAILED DESCRIPTION OF THE INVENTION

Figure 3:
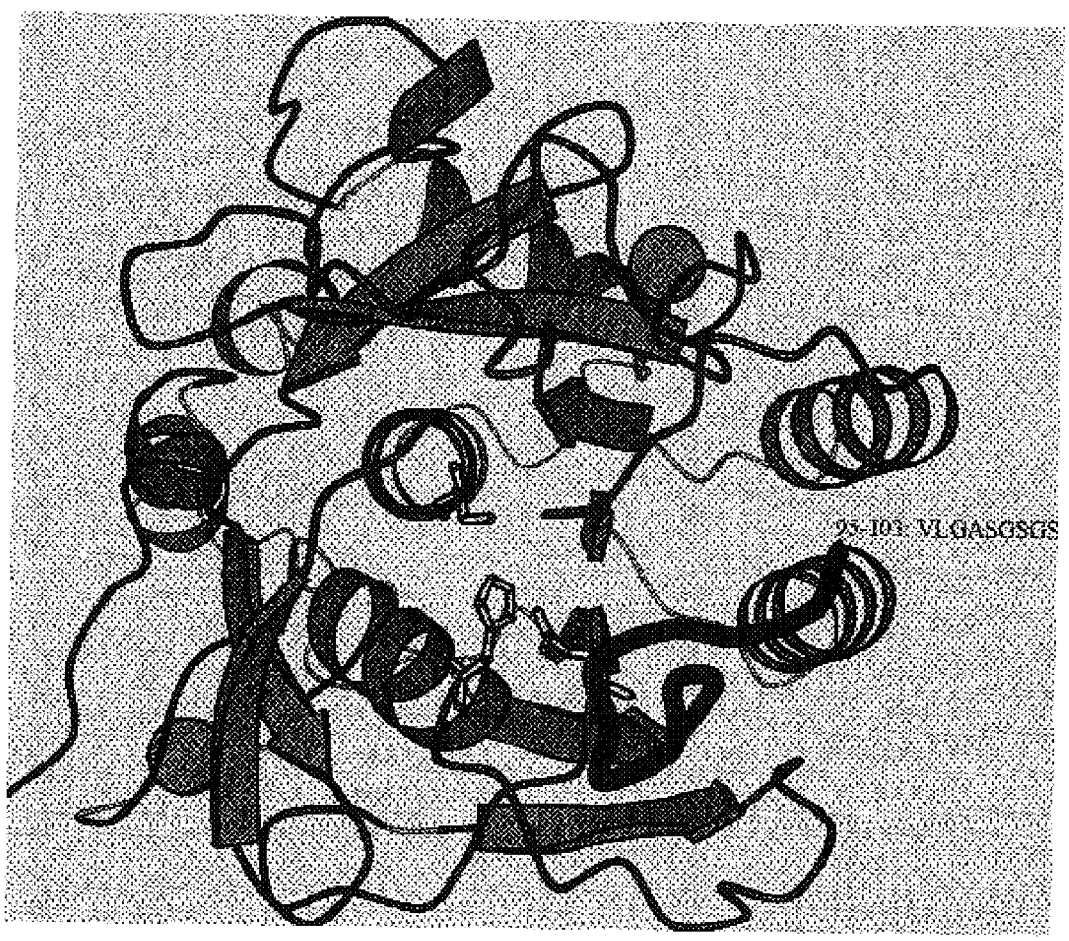
FIG. 3 shows the three dimensional structure of SAVINASE (Protein data bank (PDB) entry 1SVN), which shows the active site loop (b) region.

The subtilases of the invention in a first aspect relates to an isolated (i.e. greater than 10% pure) subtilase enzyme of the I-S1 and I-S2 sub-groups having at least one additional amino acid residue in the active site loop (b) region from positions 95 to 103, whereby said additional amino acid residue(s) correspond to the insertion of at least one amino acid residue.

In other words the subtilases of the invention are characterized by comprising an active site loop (b) region of more than 9 amino acid residues.

In a preferred embodiment, the subtilases of the present invention have at least one additional amino acid residue between positions 95 and 96.

In a preferred embodiment, the subtilases of the present invention have at least one additional amino acid residue between positions 96 and 97.

In a preferred embodiment, the subtilases of the present invention have at least one additional amino acid residue between positions 97 and 98.

In a preferred embodiment, the subtilases of the present invention have at least one additional amino acid residue between positions 98 and 99.

In a preferred embodiment, the subtilases of the present invention have at least one additional amino acid residue between positions 99 and 100.

In a preferred embodiment, the subtilases of the present invention have at least one additional amino acid residue between positions 100 and 101.

In a preferred embodiment, the subtilases of the present invention have at least one additional amino acid residue between positions 101 and 102.

In a preferred embodiment, the subtilases of the present invention have at least one additional amino acid residue between positions 102 and 103.

In a preferred embodiment, the subtilases of the present invention have at least one additional amino acid residue between positions 103 and 104.

A subtilase of the first aspect of the invention may be a parent or wild-type subtilase identified and isolated from nature.

Such a parent wild-type subtilase may be specifically screened for by standard techniques known in the art.

One preferred way of doing this may be by specifically PCR amplify DNA regions known to encode active site loops in subtilases from numerous different microorganism, preferably different Bacillus strains.

Subtilases are a group of conserved enzymes, in the sense that their DNA and amino acid sequences are homologous. Accordingly it is possible to construct relatively specific primers flanking active site loops.

One way of doing this is by investigating an alignment of different subtilases (see e.g. Siezen et al., *Protein Science*, 6, 501–523 (1997)). It is from this routine work for a person skilled in the art to construct PCR primers flanking the active site loop region corresponding to the active site loop (b) region between amino acid residues 95 to 103 in an I-S1 or I-S2 group subtilase, such as from BLSAVI. Using such PCR primers to amplify DNA from a number of different microorganism, preferably different Bacillus strains, followed by DNA sequencing of said amplified PCR fragments, it will be possible to identify strains which produce subtilases of these groups comprising a longer, as compared to e.g. BLSAVI, active site region corresponding to the active site loop (b) region from position 95 to 103. Having identified the strain and a partial DNA sequence of such a subtilase of interest, it is routine work for a person skilled in the art to complete cloning, expression and purification of such a subtilase of the invention.

However, it is envisaged that a subtilase enzyme of the invention predominantly is a variant of a parent subtilase.

Accordingly, in one embodiment the invention relates to an isolated subtilase enzyme according to the first aspect of the invention, wherein said subtilase enzyme is a constructed variant having a longer active site loop (b) region than its parent enzyme.

The subtilases of the invention exhibit excellent wash performance in a detergent, and if the enzyme is a constructed variant an improved wash performance in a detergent in comparison to its closest related subtilase, such as subtilisin 309.

Different subtilase products will exhibit a different wash performance in different types of detergent compositions. A subtilase of the invention has improved wash performance, as compared to its closest relative in a majority of such different types of detergent compositions.

Preferably, a subtilase enzyme of the invention has improved wash performance, as compared to its closest relative in the detergent compositions described in Example 3.

In order to determine if a given subtilase amino acid sequence (irrelevant whether said subtilase sequence is a parent wild-type subtilase sequence or a subtilase variant sequence produced by any other method than by site directed mutagenesis) is within the scope of the invention, the following procedure may be used:

(a) align said subtilase sequence to the amino acid sequence of subtilisin BPN';

(b) based on the alignment performed in step (a) identify the active site loop (b) region, in said subtilase sequence corresponding to the active site loop (b) region of subtilisin BPN' comprising the region between amino acid residues 95 and 103 (both of the end amino acids are included);

(c) determine if the active site loop (b) region in said subtilase sequence, identified in step (b) is longer than the corresponding active site loop in subtilisin BPN'.

If this is the case the subtilase investigated is a subtilase within the scope of the present invention.

The alignment performed in step (a) above is performed as described above by using the GAP routine.

Based on this description it is routine for a person skilled in the art to identify the active site loop (b) region in a subtilase and determine if the subtilase in question is within the scope of the invention. If a variant is constructed by site directed mutagenesis, it is of course known beforehand if the subtilase variant is within the scope of the invention.

A subtilase variant of the invention may be constructed by is standard techniques known in the art such as by site-directed/random mutagenesis or by DNA shuffling of different subtilase sequences. See sections "PRODUCING A SUBTILASE VARIANT" and "Materials and Methods" for further details.

In further embodiments the invention relates to (a) an isolated subtilase enzyme according to the invention, wherein said at least one inserted amino acid residue is chosen from the group comprising: A, G, S, and T;

(b) an isolated subtilase enzyme according to the invention, wherein said at least one inserted amino acid residue is chosen from the group of charged amino acid residues comprising: D, E, H, K, and R, more preferably D, E, K and R;

(c) an isolated subtilase enzyme according to the invention, wherein said at least one inserted amino acid residue is chosen from the group of hydrophilic amino acid residues comprising: C, N, Q, S, and T, more preferably N, Q, S and T;

(d) an isolated subtilase enzyme according to the invention, wherein said at least one inserted amino acid residue is chosen from the group of small hydrophobic amino acid residues comprising: A, G and V; or (e) an isolated subtilase enzyme according to the invention, wherein said at least one inserted amino acid residue is chosen from the group of large hydrophilic amino acid residues comprising: F, I, L, M, P, W and Y, more preferably F, I, L, M, and Y.

In a further embodiment, the invention relates to an isolated subtilase enzyme according to the invention, wherein said insertion comprises at least two amino acids, as compared to the corresponding active site loop in subtilisin BPN'.

In a further embodiment, the invention relates to one of the following subtilase enzymes comprising at least one insertion:

X95X{T,G,A,S}
X95X{D,E,K,R}
X95X{H,V,C,N,Q}
X95X{F,I,L,M,P,W,Y}
X96X{T,G,A,S}
X96X{D,E,K,R}
X96X{H,V,C,N,Q}
X96X{F,I,L,M,P,W,Y}
X97X{T,G,A,S}
X97X{D,E,K,R}
X97X{H,V,C,N,Q}
X97X{F,I,L,M,P,W,Y}
X98X{T,G,A,S}
X98X{D,E,K,R}
X98X{H,V,C,N,Q}
X98X{F,I,L,M,P,W,Y}
X99X{T,G,A,S}
X99X{D,E,K,R}
X99X{H,V,C,N,Q}
X99X{F,I,L,M,P,W,Y}
X100X{T,G,A,S}
X100X{D,E,K,R}
X100X{H,V,C,N,Q}
X100X{F,I,L,M,P,W,Y}
X101X{T,G,A,S}
X101X{D,E,K,R}
X101X{H,V,C,N,Q}
X101X{F,I,L,M,P,W,Y}
X102X{T,G,A,S}
X102X{D,E,K,R}
X102X{H,V,C,N,Q}
X102X{F,I,L,M,P,W,Y}
X103X{T,G,A,S}
X103X{D,E,K,R}
X103X{H,V,C,N,Q}
X103X{F,I,L,M,P,W,Y} or more specific for subtilisin 309 and closely related subtilases, such as BAALKP, BLSUBL, and BSKSMK

V95VA
V95VT
V95VG
V95VS
V95VD
V95VE
V95VK
V95VR

V95VH
V95VV
V95VC
V95VN
V95VQ
V95VF
V95VI
V95VL
V95VM
V95VP
V95VW
V95VY
L96LA
L96LT
L96LG
L96LS
L96LD
L96LE
L96LK
L96LR
L96LH
L96LV
L96LC
L96LN
L96LQ
L96LF
L96LI
L96LL
L96LM
L96LP
L96LW
L96LY
G97GA
G97GT
G97GG
G97GS
G97GD
G97GE
G97GK
G97GR
G97GH
G97GV
G97GC
G97GN
G97GQ
G97GF
G97GI
G97GL
G97GM
G97GP
G97GW
G97GY
A98AA
A98AT
A98AG
A98AS
A98AD
A98AE
A98AK
A98AR
A98AH
A98AV
A98AC
A98AN
A98AQ
A98AF
A98AI
A98AL
A98AM
A98AP
A98AW
A98AY
S99SA
S99ST
S99SG
S99SS
S99SD
S99SE
S99SK
S99SR
S99SH
S99SV
S99SC
S99SN
S99SQ
S99SF
S99SI
S99SL
S99SM
S99SP
S99SW
S99SY
G100GA
G100GT
G100GG
G100GS
G100GD
G100GE
G100GK
G100GR
G100GH
G100GV
G100GC
G100GN
G100GQ
G100GF
G100GI
G100GL
G100GM
G100GP
G100GW
G100GY

S101SA
S101ST
S101SG
S101SS
S101SD
S101SE
S101SK
S101SR
S101SH
S101SV
S101SC
S101SQ
S101SF
S101SI
S101SL
S101SM
S101SP
S101SW
S101SY
G102GA
G102GT
G102GG
G102GS
G102GD
G102GE
G102GK
G102GR
G102GH
G102GV
G102GC
G102GN
G102GQ
G102GF
G102GI
G102GL
G102GM
G102GP
G102GW
G102GY
S103SA
S103ST
S103SG
S103SS
S103SD
S103SE
S103SK
S103SR
S103SH
S103SV
S103SC
S103SN
S103SQ
S103SF
S103SI
S103SL
S103SM
S103SP
S103SW
S103SY

Furthermore the invention relates to subtilases comprising two or more insertions at positions 95, 96, 97, 98, 99, 100, 101, 102, or 103, including the following:
G97GAA,
G97GAS,
G97GASG (SEQ ID NO: 61),
A98ADT,
A98AGGGG (SEQ ID NO: 62),
A98AGGGS (SEQ ID NO: 63),
A98AGSGG (SEQ ID NO: 64),
A98ASGSG (SEQ ID NO: 65),
A98ASGTG (SEQ ID NO: 66),
A98ATD,
A98ATGSG (SEQ ID NO: 67),
A98ATGTG (SEQ ID NO: 68),
S99SSG, and
S101SGAA (SEQ ID NO: 69);
or any of the following combinations:
S87G+A98AGGGS (SEQ ID NO: 63),
V95VT+Y167A,
L96LA+A98T,
L96LD+A98AT,
L96LG+A98G+S99G+S101T+S103T,
L96LG+A98T+S103T,
L96LG+A98T+Y167A,
L96LG+S99T+S101A,
L96LG+G100S,
L96LG+G100S+Y167A,
L96LG+Y167A,
G97D+A98AT,
G97E+A98AT,
G97GAA+A98S+S99G,
G97GAA+A98S+S99G+S101T,
G97GAS+A98S+S99G,
G97GASG (SEQ ID NO: 61) +A98S+S99G+G100A+S101A,
G97GD+A98AT,
G97GGG+A98S+S99G,
G97K+A98AT,
G97N+A98AT,
G97Q+A98AT,
G97R+A98AT,
A98AS+A133E+T143K,
A98AT+S99SD,
A98AT+A108C+A138C,
A98AT+Y167A,
A98AT+Y167A+R170S+A194P,
A98AT+R247K,
A98G+S99A+S101ST,
A98G+G100GA+S101A+S103T,
A98G+S101SG+S103T,
A98G+S101ST,
A98GI+S99H+G100S+S101A,
A98GP+S99A, S99ASG+S101T,
S99G+G100GGT+S101T,
S99TG+S101G,
G102GT+Y167A, and
S103ST+Y167A.

It is well known in the art that a so-called conservative substitution of one amino acid residue to a similar amino acid residue is expected to produce only a minor change in the characteristic of the enzyme.

Table III below list groups of conservative amino acid substitutions.

TABLE III

Conservative amino acid substitutions

| Common Property | Amino Acid |
|---|---|
| Basic (positive charge) | K = lysine |
| | H = histidine |
| Acidic (negative charge) | E = glutamic acid |
| | D = aspartic acid |
| Polar | Q = glutamine |
| | N = asparagines |
| Hydrophobic | L = leucine |
| | I = isoleucine |
| | V = valine |
| | M = methionine |
| Aromatic | F = phenylalanine |
| | W = tryptophan |
| | Y = tyrosine |
| Small | G = glycine |
| | A = alanine |
| | S = serine |
| | T = threonine |

According to this principle, subtilase variants comprising conservative substitutions, such as G97A+A98AS+S99G and G97S+A98AT+S99A are expected to exhibit characteristics that are not drastically different from each other.

Based on the disclosed and/or exemplified subtilase variants herein, it is routine work for a person skilled in the art to identify suitable conservative modification(s) to these variants in order to obtain other subtilase variants exhibiting similarly improved wash-performance.

According to the invention, the subtilases of the invention belong to the subgroups I-S1 and I-S2, especially subgroup I-S2, both for isolating novel enzymes of the invention from nature or from the artificial creation of diversity, and for designing and producing variants from a parent subtilase.

In relation to variants from subgroup I-S1, it is preferred to choose a parent subtilase from the group comprising BS168 (BSAS, BSAPRJ, BSAPRN, BMSAMP), BASBPN, BSSDY, BLSCAR (BLKERA, BLSCA1, BLSCA2, BLSCA3), BSSPRC, and BSSPRD, or functional variants thereof having retained the characteristic of sub-group I-S1.

In relation to variants from subgroup I-S2 it is preferred to choose a parent subtilase from the group comprising BSAPRQ, BLS147 (BSAPRM, BAH101), BLSAVI (BSKSMK, BAALKP, BLSUBL), BYSYAB, and BSAPRS, or functional variants thereof having retained the characteristic of sub-group I-S2.

In particular, said parent subtilase is BLSAVI (SAVINASE®, NOVO NORDISK A/S), and a preferred subtilase variant of the invention is accordingly a variant of SAVINASE®.

The present invention also comprises any of the above mentioned subtilases of the invention in combination with any other modification to the amino acid sequence thereof, especially combinations with other modifications known in the art to provide improved properties to the enzyme are envisaged. The art describes a number of subtilase variants with different improved properties and a number of those are mentioned in the "Background of the invention" section. Those references are disclosed here as references to identify a subtilase variant, which advantageously can be combined with a subtilase variant of the invention.

Such combinations comprise positions: 222 (improve oxidation stability), 218 (improves thermal stability), substitutions in the Ca-binding sites stabilizing the enzyme, e.g. position 76, and many other apparent from the prior art.

In another embodiment, a subtilase variant of the invention may advantageously be combined with one or more modification(s) in any of the positions:
27, 36, 57, 76, 87, 97, 101, 104, 120, 123, 167, 170, 206, 218, 222, 224, 235 and 274.

Specifically the following BLSAVI, BLSUBL, BSKSMK, and BAALKP variants are considered appropriate for combination:
K27R, *36D, S57P, N76D, S87N, G97N, S101G, S103A, V104A, V104I, V104N, V104Y, H120D, N123S, Y167, R170, Q206E, N218S, M222S, M222A, T224S, K235L and T274A.

Furthermore variants comprising any of the variants K27R+V104Y+N123S+T274A, N76D+S103A+V104I, N76D+V104A, S87N+S101G+V104N, or S101G+V104N, other combinations of these mutations (K27R, N76D, S101G, V104A, V104N, V104Y, N123S, T274A) in combination with any one or more of the modification(s) mentioned above exhibit improved properties.

Even further subtilase variants of the main aspect(s) of the invention are preferably combined with one or more modification(s) in any of the positions 129, 131, 133 and 194, preferably as 129K, 131H, 133P, 133D and 194P modifications, and most preferably as P129K, P131H, A133P, A133D and A194P modifications. Any of those modification(s) are expected to provide a higher expression level of a subtilase variant of the invention in the production thereof.

Producing a Subtilase Variant

Many methods for cloning a subtilase of the invention and for introducing insertions into genes (e.g. subtilase genes) are well known in the art, cf. the references cited in the "BACKGROUND OF THE INVENTION" section.

In general standard procedures for cloning of genes and introducing insertions (random and/or site directed) into said genes may be used in order to obtain a subtilase variant of the invention. For further description of suitable techniques reference is made to the Examples and Sambrook et al. (1989) Molecular Cloning: A Laboratory Manual, Cold Spring Harbor Lab., Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for Bacillus". John Wiley and Sons, 1990); and WO 96/34946.

Further a subtilase variant of the invention may be constructed by standard techniques for artificial creation of diversity, such as by DNA shuffling of different subtilase genes (WO 95/22625; Stemmer WPC, Nature, 370, 389–91 (1994)). DNA shuffling of e.g. the gene encoding SAVINASE® with one or more partial subtilase sequences identified in nature to comprise an active site loop (b) regions longer than the active site loop (b) of SAVINASE®, will after subsequent screening for improved wash performance variants, provide subtilase variants according to the invention.

Expression Vectors

A recombinant expression vector comprising a DNA construct encoding the enzyme of the invention may be any vector which may conveniently be subjected to recombinant DNA procedures.

The choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one that on introduction into a host cell is integrated into the host cell genome in part or in its entirety and replicated together with the chromosome(s) into which it has been integrated.

The vector is preferably an expression vector in which the DNA sequence encoding the enzyme of the invention is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the enzyme.

The promoter may be any DNA sequence which shows transcriptional activity in the host cell of choice and may be derived from genes encoding proteins either homologous or heterologous to the host cell.

Examples of suitable promoters for use in bacterial host cells include the promoter of the *Bacillus stearothermophilus* maltogenic amylase gene, the *Bacillus licheniformis* alpha-amylase gene, the *Bacillus amyloliquefaciens* alpha-amylase gene, the *Bacillus subtilis* alkaline protease gene, or the *Bacillus pumilus* xylosidase gene, or the phage Lambda $P_R$ or $P_L$ promoters or the *E. coli* lac, trp or tac promoters.

The DNA sequence encoding the enzyme of the invention may also, if necessary, be operably connected to a suitable terminator.

The recombinant vector of the invention may further comprise a DNA sequence enabling the vector to replicate in the host cell in question.

The vector may also comprise a selectable marker, e.g. a gene the product of which complements a defect in the host cell, or a gene encoding resistance to e.g. antibiotics like kanamycin, chloramphenicol, erythromycin, tetracycline, spectinomycine, or the like, or resistance to heavy metals or herbicides.

To direct an enzyme of the present invention into the secretory pathway of the host cells, a secretory signal sequence (also known as is a leader sequence, prepro sequence or pre sequence) may be provided in the recombinant vector. The secretory signal sequence is joined to the DNA sequence encoding the enzyme in the correct reading frame. Secretory signal sequences are commonly positioned 5' to the DNA sequence encoding the enzyme. The secretory signal sequence may be that normally associated with the enzyme or may be from a gene encoding another secreted protein.

The procedures used to ligate the DNA sequences coding for the present enzyme, the promoter and optionally the terminator and/or secretory signal sequence, respectively, or to assemble these sequences by suitable PCR amplification schemes, and to insert them into suitable vectors containing the information necessary for replication or integration, are well known to persons skilled in the art (cf., for instance, Sambrook et al., op.cit.).

Host Cell

The DNA sequence encoding the present enzyme introduced into the host cell may be either homologous or heterologous to the host in question. If homologous to the host cell, i.e. produced by the host cell in nature, it will typically be operably connected to another promoter sequence or, if applicable, another secretory signal sequence and/or terminator sequence than in its natural environment. The term "homologous" is intended to include a DNA sequence encoding an enzyme native to the host organism in question. The term "heterologous" is intended to include a DNA sequence not expressed by the host cell in nature. Thus, the DNA sequence may be from another organism, or it may be a synthetic sequence.

The host cell into which the DNA construct or the recombinant vector of the invention is introduced may be any cell which is capable of producing the present enzyme and includes bacteria, yeast, fungi and higher eukaryotic cells including plants.

Examples of bacterial host cells which, on cultivation, are capable of producing the enzyme of the invention are gram-positive bacteria such as strains of Bacillus, such as strains of *B. alkalophilus, B. amyloliquefaciens, B. brevis, B. circulans, B. coagulans, B. lautus, B. lentus, B. licheniformis, B. megaterium, B. stearothermophilus, B. subtilis,* or *B. thuringiensis,* or strains of Streptomryces, such as *S. lividans* or *S. murinus,* or gram-negative bacteria such as *Echerichia coli.*

The transformation of the bacteria may be effected by protoplast transformation, electroporation, conjugation, or by using competent cells in a manner known per se (cf. Sambrook et al., supra).

When expressing the enzyme in bacteria such as *E. coli,* the enzyme may be retained in the cytoplasm, typically as insoluble granules (known as inclusion bodies), or may be directed to the periplasmic space by a bacterial secretion sequence. In the former case, the cells are lysed and the granules are recovered and denatured after which the enzyme is refolded by diluting the denaturing agent. In the latter case, the enzyme may be recovered from the periplasmic space by disrupting the cells, e.g. by sonication or osmotic shock, to release the contents of the periplasmic space and recovering the enzyme.

When expressing the enzyme in gram-positive bacteria such as Bacillus or Streptomryces strains, the enzyme may be retained in the cytoplasm, or may be directed to the extracellular medium by a bacterial secretion sequence. In the latter case, the enzyme may be recovered from the medium as described below.

Method of Producing Subtilase

The present invention provides a method of producing an isolated enzyme according to the invention, wherein a suitable host cell, which has been transformed with a DNA sequence encoding the enzyme, is cultured under conditions permitting the production of the enzyme, and the resulting enzyme is recovered from the culture.

When an expression vector comprising a DNA sequence encoding the enzyme is transformed into a heterologous host cell it is possible to enable heterologous recombinant production of the enzyme of the invention.

Thereby it is possible to make a highly purified subtilase composition, characterized in being free from homologous impurities.

In this context, homologous impurities mean any impurities (e.g. other polypeptides than the enzyme of the invention) which originate from the homologous cell where the enzyme of the invention is originally obtained from.

The medium used to culture the transformed host cells may be any conventional medium suitable for growing the host cells in question. The expressed subtilase may conveniently be secreted into the culture medium and may be recovered therefrom by well-known procedures including separating the cells from the medium by centrifugation or filtration, precipitating proteinaceous components of the medium by means of a salt such as ammonium sulfate, followed by chromatographic procedures such as ion exchange chromatography, affinity chromatography, or the like.

Use of a Subtilase Variant of the Invention

A subtilase protease variant of the invention may be used for a number of industrial applications, in particular within the detergent industry.

Further the invention relates to an enzyme composition, which comprises a subtilase variant of the invention.

A summary of preferred industrial applications and corresponding preferred enzyme compositions is provided below.

This summary is not in any way intended to be a complete list of suitable applications of subtilase variants of the invention. A subtilase variant of the invention may be used in other industrial applications known in the art for proteases, in particular subtilases.

Detergent Compositions Comprising the Mutant Enzymes

The present invention also relates to the use of the enzymes of the invention in cleaning and detergent compositions and compositions comprising the subtilisin enzymes. Such cleaning and detergent compositions are well described in the art, e.g., in WO 96/34946; WO 97/07202; and WO 95/30011.

Furthermore the example(s) below demonstrate the improvements in wash performance for a number of subtilase variants of the invention.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising the enzyme of the invention. The detergent additive as well as the detergent composition may comprise one or more other enzymes such as an amylase, an arabinase, a carbohydrase, a cellulase, a cutinase, a galactanase, a lipase, a mannanase, an oxidase, e.g., a laccase and/or a peroxidase, a pectinase, a protease, or a xylanase.

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

Proteases: Suitable proteases include those of animal, vegetable or microbial origin. Microbial origin is preferred. Chemically modified or protein engineered mutants are included. The protease may be a serine protease or a metalloprotease, preferably an alkaline microbial protease or a trypsin-like protease. Examples of alkaline proteases are subtilisins, especially those derived from Bacillus, e.g. subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the Fusarium protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Preferred commercially available protease enzymes include Alcalase™, SAVINASE™, Primase™, Duralase™, Esperase™, and Kannase™ (Novo Nordisk A/S), Maxatase™, Maxacal™, Maxapem™, Properase™, Purafect™, Purafect OxP™, FN2™, and FN3™ (Genencor International Inc.).

Lipases: Suitable lipases include those of bacterial or fungal origin. Chemically modified or protein engineered mutants are included. Examples of useful lipases include lipases from Humicola (synonym Thermomyces), e.g. from *H. lanuginosa* (*T. lanuginosus*) as described in EP 258 068 and EP 305 216 or from *H. insolens* as described in WO 96/13580, a Pseudomonas lipase, e.g. from *P. alcaligenes* or *P. pseudoalcaligenes* (EP 218 272), *P. cepacia* (EP 331 376), *P. stutzeri* (GB 1,372,034), *P. fluorescens*, Pseudomonas sp. strain SD 705 (WO 95/06720 and WO 96/27002), *P. wisconsinensis* (WO 96/12012), a Bacillus lipase, e.g. from *B. subtilis* (Dartois et al. (1993), Biochemica et Biophysica Acta, 1131, 253–360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include Lipolase™ and Lipolase Ultra™ (Novo Nordisk A/S).

Amylases: Suitable amylases (alpha and/or beta) include those of bacterial or fungal origin. Chemically modified or protein engineered mutants are included. Amylases include, for example, alpha-amylases obtained from Bacillus, e.g. a special strain of *B. licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are Duramyl™, Termamyl™, Fungamyl™ and BAN™ (Novo Nordisk A/S), Rapidase™ and Purastar™ (from Genencor International Inc.).

Cellulases: Suitable cellulases include those of bacterial or fungal origin. Chemically modified or protein engineered mutants are included. Suitable cellulases include cellulases from the genera Acremonium, Bacillus, Humicola, Fusarium, Pseudomonas, or Thielavia, e.g. the fungal cellulases produced from Humicola insolens, *Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299.

Commercially available cellulases include Celluzyme™, and Carezyme™ (Novo Nordisk A/S), Clazinase™, and Puradax HA™ (Genencor International Inc.), and KAC-500 (B)™ (Kao Corporation).

Peroxidases/Oxidases: Suitable peroxidases/oxidases include those of plant, bacterial or fungal origin. Chemically modified or protein engineered mutants are included. Examples of useful peroxidases include peroxidases from Coprinus, e.g. from *C. cinereus,* and variants thereof as those described in WO 93/24618, WO 95/10602, and WO 98/15257.

Commercially available peroxidases include Guardzyme™ (Novo Nordisk A/S).

The detergent enzyme(s) may be included in a detergent composition by adding separate additives containing one or more enzymes, or by adding a combined additive comprising all of these enzymes. A detergent additive of the invention, i.e. a separate additive or a combined additive, can be formulated e.g. as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0–30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0–65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly (vinylpyrrolidone), poly (ethylene glycol), poly(vinyl alcohol), poly(vinylpyridine-N-oxide), poly (vinylimidazole), polycarboxylates such as polyacrylates, maleic/acrylic acid copolymers and lauryl methacrylate/acrylic acid copolymers.

The detergent may contain a bleaching system that may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions any enzyme, in particular the enzyme of the invention, may be added in an amount corresponding to 0.01–100 mg of enzyme protein per liter of wash liquor, preferably 0.05–5 mg of enzyme protein per liter of wash liquor, in particular 0.1–1 mg of enzyme protein per liter of wash liquor.

The enzyme of the invention may additionally be incorporated in the detergent formulations disclosed in WO 97/07202 which is hereby incorporated as reference.

Leather Industry Applications

A subtilase of the invention may be used in the leather industry, in particular for use in depilation of skins.

In said application a subtilase variant of the invention is preferably used in an enzyme composition which further comprises another protease.

For a more detailed description of suitable other proteases see section relating to suitable enzymes for use in a detergent composition (vide supra).

Wool Industry Applications

A subtilase of the invention may be used in the wool industry, in particular for use in cleaning of clothes comprising wool.

In said application a subtilase variant of the invention is preferably used in an enzyme composition which further comprises another protease.

For a more detailed description of suitable other proteases see section relating to suitable enzymes for use in a detergent composition (vide supra).

The invention is described in further detail in the following examples which are not in any way intended to limit the scope of the invention as claimed.

Materials and Methods

Strains:

*B. subtilis* DN1885 (Diderichsen et al., 1990).

*B. lentus* 309 and 147 are specific strains of *Bacillus lentus,* deposited with the NCIB and accorded the accession numbers NCIB 10309 and 10147, and described in U.S. Pat. No. 3,723,250, which is incorporated herein by reference.

*E. coli* MC 1000 (M. J. Casadaban and S. N. Cohen (1980); *J. Mol. Biol.* 138 179–207), was made $r^-,m^+$ by conventional methods and is also described in U.S. patent application Ser. No. 039,298.

Plasmids:

pJS3: *E. coli-B. subtilis* shuttle vector containing a synthetic gene encoding for subtilase 309. (Described by Jacob Schiødt et al. in Protein and Peptide letters 3:39–44 (1996)).

pSX222: *B. subtilis* expression vector (Described in WO 96/34946).

General Molecular Biology Methods

Unless otherwise mentioned the DNA manipulations and transformations were performed using standard methods of molecular biology (Sambrook et al. (1989) Molecular cloning: A Laboratory Manual, Cold Spring Harbor Lab., Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for Bacillus". John Wiley and Sons, 1990).

Enzymes for DNA manipulations were used according to the specifications of the suppliers.

Enzymes for DNA Manipulations

Unless otherwise mentioned all enzymes for DNA manipulations, such as e.g. restiction endonucleases, ligases etc., are obtained from New England Biolabs, Inc.

Proteolytic Activity

In the context of this invention proteolytic activity is expressed in Kilo NOVO Protease Units (KNPU). The activity is determined relative to an enzyme standard (SAVINASE®), and the determination is based on the digestion of a dimethyl casein (DMC) solution by the proteolytic enzyme at standard conditions, i.e. 50° C., pH 8.3, 9 min. reaction time, 3 min. measuring time. A folder AF 220/1 is available upon request to Novo Nordisk A/S, Denmark, which folder is hereby incorporated by reference.

A GU is a Glycine Unit, defined as the proteolytic enzyme activity which, under standard conditions, during a 15 minute incubation at 40° C., with N-acetyl casein as substrate, produces an amount of $NH_2$-group equivalent to 1 mmole of glycine.

Protease activity can also be measured using the PNA assay with succinyl-alanine-alanine-proline-phenylalanine-paranitrophenol as the substrate. The PNA assay is further described in Rothgeb, T. M., Goodlander, B. D., Garrison, P. H., and Smith, L. A., Journal of American Oil Chemists' Society (1988).

Fermentation:

Fermentations for the production of subtilase enzymes were performed at 30° C. on a rotary shaking table (300 r.p.m.) in 500 ml baffled Erlenmeyer flasks containing 100 ml BPX medium for 5 days.

Consequently in order to make an e.g. 2 liter broth 20 Erlenmeyer flasks were fermented simultaneously.

| MEDIA: BPX Medium Composition (per liter) | |
| --- | --- |
| Potato starch | 100 g |
| Ground barley | 50 g |
| Soybean flour | 20 g |
| $Na_2HPO_4 \times 12 H_2O$ | 9 g |
| Pluronic | 0.1 g |
| Sodium caseinate | 10 g |

The starch in the medium is liquefied with alpha-amylase and the medium is sterilized by heating at 120° C. for 45 minutes. After sterilization the pH of the medium is adjusted to 9 by addition of $NaHCO_3$ to 0.1 M.

EXAMPLE 1

Construction and Expression of Enzyme Variants

Site-Directed Mutagenisis:

Subtilase 309 site-directed variants of the invention comprising specific insertions in the active site loop (b) region were made by traditional cloning of DNA fragments (Sambrook et al., Molecular Cloning: A Laboratory Manual, 2nd Ed., Cold Spring Harbor, 1989) produced by PCR of oligos containing the desired insertions (see below).

The template plasmid DNA was pJS3, or an analogue of this containing a variant of subtilase 309.

Insertions were introduced by oligo directed mutagenesis to construct DNA sequences encoding subtilase 309 variants.

DNA encoding the subtilase 309 variants was transformed into *E. coli*. DNA purified from an overnight culture of these transformants was transformed into *B. subtilis* by restriction endonuclease digestion, purification of DNA fragments, ligation, transformation of *B. subtilis*. Transformation of *B. subtilis* was performed as described by Dubnau et al., J. Mol. Biol. 56, 209–221 (1971).

Localized Random Mutagenesis in Order to Insert Random Insertions in a Localized Region:

The overall strategy used to perform localized random mutagenesis was:

A mutagenic primer (oligonucleotide) corresponding to the DNA is sequence flanking the site of insertion, separated by the DNA base pairs defining the insertion, was synthesized.

Subsequently, the resulting mutagenic primer was used in a PCR reaction with a suitable opposite primer. The resulting PCR fragment was purified and extended in a second PCR-reaction, before being digested by endonucleases and cloned into the *E. coli-B. subtilis* shuttle vector (see below).

Alternatively, and if necessary, the resulting PCR fragment is used in a second PCR reaction as a primer with a second suitable opposite primer to allow digestion and cloning of the mutagenized region into the shuttle vector. The PCR reactions are performed under normal conditions.

Following this strategy a localized random library was constructed in SAVINASE wherein insertions were introduced in the active site loop (b) region.

The mutations were introduced by mutagenic primers, so that all 20 amino acids were represented (N=25% of A, T, C, and G; whereas S=50% C and G. The produced PCR fragment was extended towards the N-terminal of SAVINASE by another round of PCR by combination of an overlapping sequence with a PCR-fragment produced by PCR-amplification with primers.

For insertions between positions 95 and 96, the primers used were 5'-CTA AAT ATT CGT GGTGGC GC-3' (sense) (SEQ ID NO: 7) and 5'-GAC TTT AAC AGC GTA TAG CTC AGC-3' (antisense) (SEQ ID NO: 8). For insertions between positions 96 and 97, the primers used were 5'-CTA AAT ATT CGT GGTGGC GC-3' (sense) (SEQ ID NO: 9) and 5'-GAC TTT AAC AGC GTA TAG CTC AGC-3' (antisense) (SEQ ID NO: 10). For insertions between positions 97 and 98, the primers used were 5'-CTA AAT ATT CGT GGT GGC GC-3' (sense) (SEQ ID NO: 11) and 5'-GAC TTT AAC AGC GTA TAG CTC AGC-3' (antisense) (SEQ ID NO: 12). For insertions between positions 98 and 99, the primers used were 5'-CTA AAT ATT CGT GGTGGC GC-3' (sense) (SEQ ID NO: 13) and 5'-GAC TTT AAC AGC GTA TAG CTC AGC-3' (antisense) (SEQ ID NO: 14). For insertions between positions 99 and 100, the primers used were 5'-CTA AAT ATT CGT GGTGGC GC-3' (sense) (SEQ ID NO: 15) and 5'-GAC TTT AAC AGC GTA TAG CTC AGC-3' (antisense) (SEQ ID NO: 16). For insertions between positions 100 and 101, the primers used were 5'-CTA AAT ATT CGT GGTGGC GC-3' (sense) (SEQ ID NO: 17) and 5'-GAC TTT AAC AGC GTA TAG CTC AGC-3' (antisense) (SEQ ID NO: 18). For insertions between positions 101 and 102, the primers used were 5'-CTA AAT ATT CGT GGTGGC GC-3' (sense) (SEQ ID NO: 19) and 5'-GAC TTT AAC AGC GTA TAG CTC AGC-3' (antisense) (SEQ ID NO: 20). For insertions between positions 102 and 103, the primers used were 5'-CTA AAT ATT CGT GGTGGC GC-3' (sense) (SEQ ID NO: 21) and 5'-GAC TTT AAC AGC GTA TAG CTC AGC-3' (antisense) (SEQ ID NO: 22). For insertions between positions 103 and 104, the primers used were 5'-CTA AAT ATT CGT GGTGGC GC-3' (sense) (SEQ ID NO: 23) and 5'-GAC TTT AAC AGC GTA TAG CTC AGC-3' (antisense) (SEQ ID NO: 24).

The extended DNA fragments were cloned into the Hind III- and Mlu I-sites of the modified plasmid pJS3 (see above), and ten randomly chosen E. coli colonies were sequenced to confirm the mutations designed.

For insertions between positions 95 and 96, the mutagenic primer 5'-GCT GAG CTA TAC GCT GTT AAA GTC NNS CTA GGG GCG AGC GGT TCA GGT TC-3' (sense) (SEQ ID NO: 25) was used in a PCR reaction with a suitable anti-sense opposite primer, situated downstream of the Mlu I site in pJS3 (e.g. 5'-CCC TTT AAC CGC ACA GCG TTT-3' (anti-sense) (SEQ ID NO: 26)) and the plasmid pJS3 as template. For insertions between positions 96 and 97, the mutagenic primer 5'-GCT GAG CTA TAC GCT GTT AAA GTC CTA NNS GGG GCG AGC GGT TCA GGT TC 3' (sense) (SEQ ID NO: 27) was used in a PCR reaction with a suitable anti-sense opposite primer, situated downstream of the Mlu I site in pJS3 (e.g. 5'-CCC TTT AAC CGC ACA GCG TTT-3' (anti-sense) (SEQ ID NO: 28)) and the plasmid pJS3 as template. For insertions between positions 97 and 98, the mutagenic primer 5'-GCT GAG CTA TAC GCT GTT AAA GTC CTA GGG NNS GCG AGC GGT TCA GGT TC 3' (sense) (SEQ ID NO: 29) was used in a PCR reaction with a suitable anti-sense opposite primer, situated downstream of the Mlu I site in pJS3 (e.g. 5'-CCC TTT AAC CGC ACA GCG TTT-3' (anti-sense) (SEQ ID NO: 30)) and the plasmid pJS3 as template. For insertions between positions 98 and 99, the mutagenic primer 5'-GCT GAG CTA TAC GCT GTT AAA GTC CTA GGG GCG NNS AGC GGT TCA GGT TCG GTC AGC-3' (sense) (SEQ ID NO: 31) was used in a PCR reaction with a suitable anti-sense opposite primer, situated downstream of the Mlu I site in pJS3 (e.g. 5'-CCC TTT AAC CGC ACA GCG TTT-3' (anti-sense) (SEQ ID NO: 32)) and the plasmid pJS3 as template. For insertions between positions 99 and 100, the mutagenic primer 5'-GTT AAA GTC CTA GGG GCG AGC NNS GGT TCA GGT TCG GTC AGC TCG-3' (sense) (SEQ ID NO: 33) was used in a PCR reaction with a suitable anti-sense opposite primer, situated downstream of the Mlu I site in pJS3 (e.g. 5'-CCC TTT AAC CGC ACA GCG TTT-3' (anti-sense) (SEQ ID NO: 34)) and the plasmid pJS3 as template. For insertions between positions 100 and 101, the mutagenic primer 5'-GTT AAA GTC CTA GGG GCG AGC GGT NNS TCA GGT TCG GTC AGC TCG ATT G-3' (sense) (SEQ ID NO: 35) was used in a PCR reaction with a suitable anti-sense opposite primer, situated downstream of the Mlu I site in pJS3 (e.g. 5'-CCC TTT AAC CGC ACA GCG TTT-3' (anti-sense) (SEQ ID NO: 36)) and the plasmid pJS3 as template. For insertions between positions 101 and 102, the mutagenic primer 5'-GTC CTA GGG GCG AGC GGT TCA NNS GGT TCG GTC AGC TCG ATT GCC-3' (sense) (SEQ ID NO: 37) was used in a PCR reaction with a suitable anti-sense opposite primer, situated downstream of the Mlu I site in pJS3 (e.g. 5'-CCC TTT AAC CGC ACA GCG TTT-3' (anti-sense) (SEQ ID NO: 38)) and the plasmid pJS3 as template. For insertions between positions 102 and 103, the mutagenic primer 5'-CTA GGG GCG AGC GGT TCA GGT NNS TCG GTC AGC TCG ATT GCC CAA G-3' (sense) (SEQ ID NO: 39) was used in a PCR reaction with a suitable anti-sense opposite primer, situated downstream of the Mlu I site in pJS3 (e.g. 5'-CCC TTT AAC CGC ACA GCG TTT-3' (anti-sense) (SEQ ID NO: 40)) and the plasmid pJS3 as template. For insertions between positions 103 and 104, the mutagenic primer 5'-CTA GGG GCG AGC GGT TCA GGT TCG NNS GTC AGC TCG ATT GCC CAA GGA TTG-3' (sense) (SEQ ID NO: 41) was used in a PCR reaction with a suitable anti-sense opposite primer, situated downstream of the Mlu I site in pJS3 (e.g. 5'-CCC TTT AAC CGC ACA GCG TTT-3' (anti-sense) (SEQ ID NO: 42)) and the plasmid pJS3 as template.

The resulting PCR products were cloned into the pJS3 shuttle is vector by using the restriction enzymes Hind III and Mlu I.

The random library was transformed into E. coli by well known techniques.

The library prepared contained approximately 100,000 individual clones/library.

Ten randomly chosen colonies were sequenced to confirm the mutations designed.

In order to purify a subtilase variant of the invention, the B. subtilis pJS3 expression plasmid comprising a variant of the invention was transformed into a competent B. subtilis strain and was fermented as described above in a medium containing 10 micrograms/ml Chloramphenicol (CAM).

EXAMPLE 2

Purification of Enzyme Variants

This procedure relates to purification of a two liter scale fermentation for the production of the subtilases of the invention in a Bacillus host cell.

Approximately 1.6 liters of fermentation broth were centrifuged at 5000 rpm for 35 minutes in 1 liter beakers. The supernatants were adjusted to pH 6.5 using 10% acetic acid and filtered on Seitz Supra S100 filter plates.

The filtrates were concentrated to approximately 400 ml using an Amicon CH2A UF unit equipped with an Amicon S1Y10 UF cartridge. The UF concentrate was centrifuged and filtered prior to absorption at room temperature on a Bacitracin affinity column at pH 7. The protease was eluted from the Bacitracin column at room temperature using 25% 2-propanol and 1 M sodium chloride in a buffer solution with 0.01 dimethylglutaric acid, 0.1 M boric acid and 0.002 M calcium chloride adjusted to pH 7.

The fractions with protease activity from the Bacitracin purification step were combined and applied to a 750 ml Sephadex G25 column (5 cm dia.) equilibrated with a buffer containing 0.01 dimethylglutaric acid, 0.2 M boric acid and 0.002 M calcium chloride adjusted to pH 6.5.

Fractions with proteolytic activity from the Sephadex G25 column were combined and applied to a 150 ml CM Sepharose CL 6B cation exchange column (5 cm dia.) equilibrated with a buffer containing 0.01 M dimethylglutaric acid, 0.2 M boric acid, and 0.002 M calcium chloride adjusted to pH 6.5.

The protease was eluted using a linear gradient of 0–0.1 M sodium chloride in 2 liters of the same buffer (0–0.2 M sodium chloride in case of subtilisin 147).

In a final purification step protease containing fractions from the CM Sepharose column were combined and concentrated in an Amicon ultrafiltration cell equipped with a GR81PP membrane (from the Danish Sugar Factories Inc.).

By using the techniques of Example 1 for the construction and fermentation, and the above isolation procedure the following subtilisin 309 variants were produced and isolated:

V95VT
V95VS
V95VD
V95VE
V95VP
V95VG
V95VH
V95VI
V95VT + Y167A
L96LT
L96LS
L96LD
L96LE
L96LP
L96LG
L96LH
L96LI
L96LA
L96LG
L96LA + A98T
L96LT + Y167A
L96LG + G100S
L96LG + A98T + Y167A
L96LG + A98T + S103T
L96LA + A98T + A194P
L96LG + S99T + S101A
L96LG + G100S + Y167A
N76D + L96LA + A98T
L96LG + A98G + S99G + S101T + S103T
G97GT
G97GS
G97GD
G97GE
G97GP
G97GG
G97GH
G97GI
G97GA
G97GT + Y167A
G97GP + A98T
A98AT
A98AS
A98AD
A98AE
A98AP
A98AG
A98AH
A98AI
A98AT + Y167A
A98AD
A98AG
A98AH
A98AI
A98AN
A98AP
A98AS
A98AT
A98AV
A98AY
A98SD
A98TP
A98TW
A98ASGTG (SEQ ID NO: 66)
A98ATGSG (SEQ ID NO: 67)
A98ATGTG (SEQ ID NO: 68)
A98AGGGG (SEQ ID NO: 62)
A98AGSGG (SEQ ID NO: 64)
A98AT + Y167A
A98AT + R247K

-continued
A98GP + S99A
G97D + A98AT
G97E + A98AT
G97K + A98AT
G97N + A98AT
G97Q + A98AT
G97R + A98AT
S87G + A98AGGGS (SEQ ID NO: 63)
A98A5 + A133E + T143K
A98AT + A108C+ A138C
A98AT + Y167A + R170S + A194P
A98GI + S99H + G100S + S101A
S99ST
S99SS
S99SD
S99SE
S99SP
S99SG
S99SH
S99SI
S99SA
S99TP
S99TK
S99TN
S99TQ
S99TR
S99SSG
S99ST + Y167A
S99TG + S101G
S99ASG + S101T
S99TC + S101C
A98G + S99SQ
G100GT
G100GA
G100GS
G100GD
G100GE
G100GP
G100GG
G100GH
G100GI
G100GT + Y167A
S99G + G100GT + S101T
A98G + G100GA + S101A + S103T
S101ST
S101SS
S101SA
S101SD
S101SE
S101SP
S101SG
S101SH
S101SI
S101SGAA (SEQ ID NO: 69)
S101ST + Y167A
A98G + S101ST
A98G + S101SG + S103T
A98G + S99A + S101ST
G102GT
G102GS
G102GA
G102GD
G102GE
G102GP
G102GG
G102GH
G102GI
G102GT + Y167A
S103ST
S103SA
S103SS
S103SD
S103SE
S103SP
S103SG
S103SH
S103SI
S103ST + Y167A These variants were found to exhibit better wash performance than SAVINASE in a preliminary assay.

EXAMPLE 3

Wash Performance of Detergent Compositions Comprising Enzyme Variants

The following examples provide results from a number of washing tests that were conducted under the conditions indicated.

Mini Wash

Wash Conditions:

|  | Europe | Detergent 95 | US |
|---|---|---|---|
| Detergent Dosage | 4 g/l | 3 g/l | 1 g/l |
| Wash Temp | 30° C. | 15° C. | 25° C. |
| Wash Time | 30 min | 15 min | 10 min |
| Water hardness | 18° dH ($Ca^{2+}/Mg^{2+}$ = 5:1) | 6° dH | 6° dH ($Ca^{2+}/Mg^{2+}$ = 2:1) |
| pH | Not adjusted | 10.5 | Not adjusted |
| Enzyme conc. | 1, 2, 5, 10, 30 nM |  | 1, 2, 5, 10, 30 nM |
| Test system | 150 ml glass beakers with a stirring rod | 10 nm | 150 ml glass beakers with a stirring rod |
| Textile/volume | 5 textile pieces (Ø 2.5 cm) in 50 ml detergent | 5 textile pieces (Ø 2.5 cm) in 50 ml detergent | 5 textile pieces (Ø 2.5 cm) in 50 ml detergent |
| Test Material | EMPA116 | EMPA117 | EMPA117 |

Detergents:

The detergents used were either a model detergent, named Detergent 95, or obtained from supermarkets in Denmark (OMO, datasheet ED-9745105) and the USA (Wisk, datasheet ED-9711893), respectively. Prior to use, all enzymatic activity in the detergents was inactivated by microwave treatment.

Detergent 95 is a simple model formulation. pH is adjusted to 10.5 which is within the normal range for a powder detergent. The composition of model detergent 95 is as follows:

| 25% | STP ($Na_5P_3O_{10}$) |
|---|---|
| 25% | $Na_2SO_4$ |
| 10% | $Na_2CO_3$ |
| 20% | LAS (Nansa 80S) |
| 5.0% | Nonionic tenside (Dobanol 25-7) |
| 5.0% | $Na_2Si_2O_5$ |
| 0.5% | Carboxymethylcellulose (CMC) |
| 9.5% | Water |

Swatches:

The swatches used were EMPA116 and EMPA117, obtained from EMPA Testmaterialen, Movenstrasse 12, CH-9015 St. Gall, Switzerland.

Reflectance

Measurement of reflectance (R) on the test material was done at 460 nm using a Macbeth ColorEye 7000 photometer. The measurements were done according to the manufacturer's protocol.

Evaluation

The evaluation of the wash performance of a subtilase is determined by either the improvement factor or the performance factor for the subtilase investigated.

The improvement factor, $IF_{Dose/response}$, is defined as the ratio between the slopes of the wash performance curves for a detergent containing the subtilase investigated and the same detergent containing a reference subtilase at the asymptotic concentration of the subtilase goes to zero $$IF_{Dose/response} = a/a_{ref}$$

The wash performance is calculated according to the formula I:

$$R = R_0 + (a\ \text{delta}R_{max}\ c)/(\text{delta}R_{max} + a\ c)$$

where

R is the wash performance in reflectance units; $R_0$ is the intercept of the fitted curve with y-axis (blind); a is the slope of the fitted curve as c→0; c is the enzyme concentration; and delta$R_{max}$ is the theoretical maximal wash effect as c→∞.

The performance factor, P, is calculated according to formula II $$P = (R_{variant} - R_{blank})/(R_{SAVINASE} - R_{blank}) \quad (ii)$$

where $R_{variant}$ is the reflectance of test material washed with 10 nM variant; $R_{SAVINASE}$ is the reflectance of test material washed with 10 nM SAVINASE; $R_{blank}$ is the reflectance of test material washed with no enzyme.

Model Detergent 95

| Variant | P |
|---|---|
| L96LG + A98G + S99G + S101T + S103T | 1.3 |
| L96LG + S99T + S101A | 1.2 |
| L96LG + A98T + S103T | 1.3 |
| S99ASG + S101T | 1.4 |
| S99TG + S101G | 1.3 |

US (Detergent: OMO, Swatch: EMPA116)

| Variant | $IF_{Dose/response}$ | P |
|---|---|---|
| G97GA | 2.2 | — |

US (detergent: US Wisk, Swatch: EMPA117)

| Variant | $IF_{Dose/response}$ | P |
|---|---|---|
| V95VT | >3 | 2.3 |
| L96LG | — | 1.7 |
| L96LA | — | 1.4 |
| L96LG | — | 1.4 |
| L96LT | — | 1.5 |
| L96LA + A98T | — | 2.2 |
| L96LG + G100S | — | 1.8 |
| L96LG + Y167A | — | 2.0 |
| L96LA + A98T | — | 1.3 |
| L96LG + A98T + S103T | — | 1.3 |
| L96LA + A98T + A194P | — | 1.2 |
| L96LG + S99T + S101A | — | 1.2 |
| N76D + L96LA + A98T | — | 1.3 |
| L96LG + A98G + S99G + S101T + S103T | — | 1.7 |
| G97GA | — | 1.42 |
| G97GP + A98T | — | 1.51 |

-continued

| Variant | IF$_{Dose}$/response | P |
|---|---|---|
| G97GAA + A98S + A98S + S99G + S101T | — | 1.28 |
| A98AT | >3 | 2.3 |
| A98AD | — | 1.2 |
| A98AG | — | 1.1 |
| A98AH | — | 1.4 |
| A98AI | — | 1.2 |
| A98AN | — | 1.0 |
| A98AP | — | 1.3 |
| A98AS | — | 1.6 |
| A98AV | — | 1.1 |
| A98AY | — | 1.1 |
| A98SD | — | 1.2 |
| A98TP | — | 1.5 |
| A98TW | — | 1.2 |
| A98AGGGG (SEQ ID NO: 62) | — | 1.1 |
| A98ASGTG (SEQ ID NO: 66) | — | 1.1 |
| A98ATGSG (SEQ ID NO: 67) | — | 1.3 |
| A98ATGTG (SEQ ID NO: 68) | — | 1.2 |
| A98AGSGG (SEQ ID NO: 64) | — | 1.7 |
| A98AT + Y167A | — | 1.7 |
| A98AT + R247K | — | 1.3 |
| A98GP + S99A | — | 1.1 |
| G97D + A98AT | — | 1.4 |
| G97E + A98AT | — | 1.6 |
| G97K + A98AT | — | 1.0 |
| G97N + A98AT | — | 1.2 |
| G97Q + A98AT | — | 1.0 |
| G97R + A98AT | — | 1.0 |
| S87G + A98AGGGS (SEQ ID NO: 63) | — | 1.2 |
| A98AS + A133E + T143K | — | 0.8 |

-continued

| Variant | IF$_{Dose}$/response | P |
|---|---|---|
| A98AT + A108C + A138C | — | 1.2 |
| A98AT + Y167A + R 170S + A194P | — | 1.3 |
| A98GI + S99H + G100S + S101A | — | 1.0 |
| S99SA | — | 1.4 |
| S99TP | — | 1.1 |
| S99TK | — | 1.0 |
| S99TN | — | 1.7 |
| S99TR | — | 1.1 |
| S99TQ | — | 1.5 |
| S99SSG | — | 2.3 |
| S99ASG + S101T | — | 2.1 |
| S99TC + S101C | — | 0.7 |
| S99TG + S101G | — | 1.5* |
| A98G + S99SQ | — | 1.2 |
| G100GA | — | 1.2 |
| S99G + G100GGT + S101T | — | 1.6 |
| S101ST | — | 1.6 |
| S101SA | — | 1.3 |
| S101SGAA (SEQ ID NO: 69) | — | 1.5* |
| A98G + S101SG + 5103T | — | 1.0 |
| A98G + S99A + S101ST | — | 1.3 |
| G102GA | — | 1.3 |
| G102GT | >3 | 2.3 |
| S103SA | — | 1.3 |
| S103ST | >3 | 2.3 |

*P calculated at [E] = 5 nM

The results show that subtilases of the invention exhibit improved wash performance in comparison to SAVINASE®.

What is claimed is:

1. A modified subtilase comprising a mutation in an amino acid sequence of a subtilase, wherein the mutation is an insertion of one or more amino acid residues at position 95 of the active site loop (b) region corresponding to positions 95 to 103, wherein the positions are numbered according to the amino acid sequence of the mature subtilisin BPN' of SEQ ID NO: 4.

2. The modified subtilase of claim 1, wherein the one or more amino acid residues are A, G, S or T.

3. The modified subtilase of claim 1, wherein the one or more amino acid residues are D, E, H, K or R.

4. The modified subtilase of claim 1, wherein the one or more amino acid residues are C, N, Q, S or T.

5. The modified subtilase of claim 1, wherein the one or more amino acid residues are A, G or V.

6. The modified subtilase of claim 1, wherein the one or more amino acid residues are F, I, L, M, P, W or Y.

7. The modified subtilase of claim 1, wherein the mutation comprises; V95VA, V95VC, V95VD, V95VE, V95VF, V95VG, V95VH, V95VI, V95VK, V95VL, V95VM, V95VN, V95VP, V95VQ, V95VR, V95VS, V95VT, V95VV, V95VW, or V95VY.

8. The modified subtilase of claim 1, comprising V95VT+Y167A.

9. The modified subtilase of claim 1, wherein the mutation is an insertion of two or more amino acid residues at position 95.

10. The modified subtilase of claim 1, comprising at least one further mutation at one or more positions.

11. The modified subtilase of claim 10, wherein the one or more positions are selected from the group consisting of 27, 36, 57, 76, 87, 97, 101, 104, 120, 123, 167, 170, 206, 218, 222, 224, 235 and 274.

12. The modified subtilase of claim 11, wherein the at least one further mutation is selected from the group consisting of K27R, *36D, S57P, N76D, S87N, G97N, S101G, V104A, V104N, V104Y, H120D, N123S, Y167X, R170X, Q206E, N218S, M222A, M222S, T224S, K235L, and T274A.

13. The modified subtilase of claim 12, wherein the at least one further mutation is selected from the group consisting of K27R+V104Y+N123S+T274A, N76D+S103A+V104I, N76D+V104A, S87N+S101G+V104N, S101G+V104N, and any other combination of K27R, N76D, S101G, V104A, V104N, V104Y, N123S, and T274A.

14. The modified subtilase of claim 10, wherein the one or more positions are selected from the group consisting of 129, 131, 133 and 194.

15. The modified subtilase of claim 14, wherein the at least one further mutation is selected from the group consisting of P129K, P131H, A133D, A133P, and A194P.

16. The modified subtilase of claim 1, wherein the subtilase is a sub-group I-S1 subtilase.

17. The modified subtilase of claim 16, wherein the subtilase is selected from the group consisting of subtilisin I168, subtilisin BPN', subtilisin DY, and subtilisin Carlsberg.

18. The modified subtilase of claim 1, wherein the subtilase is a sub-group I-S2 subtilase.

19. The modified subtilase of claim 18, wherein the subtilase is subtilisin 147, subtilisin 309, subtilisin PB92, and subtilisin YaB.

20. A composition comprising a modified subtilase of claim 1 and a surfactant.

21. The composition of claim 20, further comprising an amylase, cellulase, cutinase, lipase, oxidoreductase, or another protease.

22. An isolated DNA sequence encoding a modified subtilase of claim 1.

23. An expression vector comprising an isolated DNA sequence of claim 21.

24. A microbial host cell transformed with an expression vector of claim 22.

25. A method for producing a modified subtilase, comprising
    (a) culturing a microbial host cell of claim 24 under conditions conducive to the expression and secretion of the modified subtilase, and
    (b) recovering the modified subtilase.

26. A modified subtilase comprising a mutation in an amino acid sequence of a subtilase, wherein the mutation is an insertion of one or more amino acid residues at position 96 of the active site loop (b) region corresponding to positions 95 to 103, wherein the positions are numbered according to the amino acid sequence of the mature subtilisin BPN' of SEQ ID NO: 4.

27. The modified subtilase of claim 26, wherein the one or more amino acid residues are A, G, S, or T.

28. The modified subtilase of claim 26, wherein the one or more amino acid residues are D, E, H, K, or R.

29. The modified subtilase of claim 26, wherein the one or more amino acid residues are C, N, Q, S or T.

30. The modified subtilase of claim 26, wherein the one or more amino acid residues are A, G or V.

31. The modified subtilase of claim 26, wherein the one or more amino acid residues are F, I, L, M, P, W or Y.

32. The modified subtilase of claim 26, wherein the mutation comprises: L96LA, L96LC, L96LD, L96LE, L96LF, L96LG, L96LH, L96LI, L96LK, L96LL, L96LM, L96LN, L96LP, L96LQ, L96LR, L96LS, L96LT, L96LV, L96LW, or L96LY.

33. The modified subtilase of claim 26, comprising:
    N76D+L96LA+A98T,
    L96LA+A98T,
    L96LA+A98T+A194P,
    L96LG+A98G+S99G+S101T+S103T,
    L96LG+A98T+S103T,
    L96LG+A98T+Y167A,
    L96LG+S99T+S101A,
    L96LG+G100S,
    L96LG+G100S+Y167A, or
    L96LG+Y167A.

34. The modified subtilase of claim 26, wherein the mutation is an insertion of two or more amino acid residues at position 95.

35. The modified subtilase of claim 26, comprising at least one further mutation at one or more positions.

36. The modified subtilase of claim 35, wherein the one or more positions are selected from the group consisting of: 27, 36, 57, 76, 87, 97, 101, 104, 120, 123, 167, 170, 206, 218, 222, 224, 235 and 274.

37. The modified subtilase of claim 36, wherein the at least one further mutation is selected from the group consisting of K27R, *36D, S57P, N76D, S87N, G97N, S101G, V104A, V104N, V104Y, H120D, N123S, Y167X, R170X, Q206E, N218S, M222A, M222S, T224S, K235L, and T274A.

38. The modified subtilase of claim 37, wherein the at least one further mutation is selected from the group consisting of K27R+V104Y+N123S+T274A, N76D+S103A+V104I, N76D+V104A, S87N+S101G+V104N, S101G+V104N, and any other combination of K27R, N76D, S101G, V104A, V104N, V104Y, N123S, and T274A.

39. The modified subtilase of claim 35, wherein the one or more positions are selected from the group consisting of 129, 131, 133 and 194.

40. The modified subtilase of claim 39, wherein the at least one further mutation is selected from the group consisting of P129K, P131H, A133D, A133P, and A194P.

41. The modified subtilase of claim 26, wherein the subtilase is a subtilase of sub-group I-S1.

42. The modified subtilase of claim 41, wherein the subtilase is selected from the group consisting of subtilisin I168, subtilisin BPN', subtilisin DY, and subtilisin Carlsberg.

43. The modified subtilase of claim 26, wherein the subtilase is a subtilase of sub-group I-S2.

44. The modified subtilase of claim 43, wherein the subtilase is selected from the group consisting of subtilisin 147, subtilisin 309, subtilisin PB92, and subtilisin YaB.

45. A composition comprising a modified subtilase of claim 26 and a surfactant.

46. The composition of claim 45, which additionally comprises an amylase, cellulase, cutinase, lipase, oxidoreductase, or another protease.

47. A DNA sequence encoding a modified subtilase of claim 26.

48. An expression vector comprising a DNA sequence of claim 47.

49. A microbial host cell transformed with an expression vector of claim 48.

50. A method for producing a modified subtilase, comprising
    (a) culturing a microbial host cell of claim 49 under conditions conducive to the expression and secretion of the modified subtilase, and
    (b) recovering the modified subtilase.

51. A modified subtilase comprising a mutation in an amino acid sequence of a subtilase, wherein the mutation is an insertion of one or more amino acid residues at position 97 of the active site loop (b) region corresponding to positions 95 to 103, wherein the positions are numbered according to the amino acid sequence of the mature subtilisin BPN' of SEQ ID NO: 4.

52. The modified subtilase of claim 51, wherein the one or more amino acid residues are A, G, S, or T.

53. The modified subtilase of claim 51, wherein the one or more amino acid residues are D, E, H, K, or R.

54. The modified subtilase of claim 51, wherein the one or more amino acid residues are C, N, Q, S or T.

55. The modified subtilase of claim 51, wherein the one or more amino acid residues are A, G or V.

56. The modified subtilase of claim 51, wherein the one or more amino acid residues are F, I, L, M, P, W or Y.

57. The modified subtilase of claim 51, wherein the mutation comprises: G97GA, G97GC, G97GD, G97GE, G97GF, G97GG, G97GH, G97GI, G97GK, G97GL, G97GM, G97GN, G97GP, G97GQ, G97GR, G97GS, G97GT, G97GV, G97GW, or G97GY.

58. The modified subtilase of claim 51, comprising

G97GA,

G97GP+A98T, or

G97GT+Y167A.

59. The modified subtilase of claim 58, wherein the mutation is an insertion of two or more amino acid residues at position 97.

60. The modified subtilase of claim 51, comprising at least one further mutation at one or more positions.

61. The modified subtilase of claim 60, wherein the one or more positions are selected from the group consisting of 27, 36, 57, 76, 87, 97, 101, 104, 120, 123, 167, 170, 206, 218, 222, 224, 235 and 274.

62. The modified subtilase of claim 61, wherein the at least one further mutation is selected from the group consisting of K27R, *36D, S57P, N76D, S87N, G97N, S101G, V104A, V104N, V104Y, H120D, N123S, Y167X, R170X, Q206E, N218S, M222A, M222S, T224S, K235L, and T274A.

63. The modified subtilase of claim 62, wherein the at least one further mutation is selected from the group consisting of K27R+V104Y+N123S+T274A, N76D+S103A+V104I, N76D+V104A, S87N+S101G+V104N, S101G+V104N, and any other combination of K27R, N76D, S101G, V104A, V104N, V104Y, N123S, and T274A.

64. The modified subtilase of claim 60, wherein the one or more positions are selected from the group consisting of 129, 131, 133 and 194.

65. The modified subtilase of claim 64, wherein the at least one further mutation is selected from the group consisting of P129K, P131H, A133D, A133P, and A194P.

66. The modified subtilase of claim 51, wherein the subtilase is a sub-group I-S1 subtilase.

67. The modified subtilase of claim 66, wherein the subtilase is selected from the group consisting of subtilisin I168, subtilisin BPN', subtilisin DY, and subtilisin Carlsberg.

68. The modified subtilase of claim 51, wherein the subtilase is a sub-group I-S2 subtilase.

69. The modified subtilase of claim 68, wherein the subtilase is subtilisin 147, subtilisin 309, subtilisin PB92, and subtilisin YaB.

70. A composition comprising a modified subtilase of claim 51 and a surfactant.

71. The composition of claim 70, which additionally comprises an amylase, cellulase, cutinase, lipase, oxidoreductase, or another protease.

72. A DNA sequence encoding a modified subtilase of claim 51.

73. An expression vector comprising a DNA sequence of claim 72.

74. A microbial host cell transformed with an expression vector of claim 73.

75. A method for producing a modified subtilase, comprising (a) culturing a microbial host cell of claim 74 under conditions conducive to the expression and secretion of the modified subtilase, and (b) recovering the modified subtilase.

76. A modified subtilase comprising a mutation in an amino acid sequence of a subtilase, wherein the mutation is an insertion of one or more amino acid residues at position 98 of the active site loop (b) region corresponding to positions 95 to 103, wherein the positions are numbered according to the amino acid sequence of the mature subtilisin BPN' of SEQ ID NO: 4.

77. The modified subtilase of claim 76, wherein the one or more amino acid residues are A, G, S, or T.

78. The modified subtilase of claim 76, wherein the one or more amino acid residues are D, E, H, K, or R.

79. The modified subtilase of claim 76, wherein the one or more amino acid residues are C, N, Q, S or T.

80. The modified subtilase of claim 76, wherein the one or more amino acid residues are A, G or V.

81. The modified subtilase of claim 76, wherein the one or more amino acid residues are F, I, L, M, P, W or Y.

82. The modified subtilase of claim 76, wherein the mutation comprises: A98AA, A98AC, A98AD, A98AE, A98AF, A98AG, A98AH, A98AI, A98AK, A98AL, A98AM, A98AN, A98AP, A98AQ, A98AR, A98AS, A98AT, A98AV, A98AW, or A98AY.

83. The modified subtilase of claim 76, wherein the mutation results in an insertion of two or more amino acid residues at position 98.

84. The modified subtilase of claim 76, which comprises:

A98SD,

A98TP, or

A98TW.

85. The modified subtilase of claim 76, which comprises:

S87G+A98AGGGS (SEQ ID NO: 63),

L96LD+A98AT,

G97D+A98AT,

G97E+A98AT,

G97GD+A98AT,

G97K+A98AT,

G97N+A98AT,

G97Q+A98AT,

G97R+A98AT,

A98ADT,

A98AGGGG (SEQ ID NO: 62),

A98AGGGS (SEQ ID NO: 63),

A98AGSGG (SEQ ID NO: 64),

A98AS+A133E+T143K,

A98ASGSG (SEQ ID NO: 65),

A98ASGTG (SEQ ID NO: 66),

A98AT+S99SD,

A98AT+A108C+A138C,

A98AT+Y167A,

A98AT+Y167A+R170S+A194P,

A98AT+R247K,

A98ATD,

A98ATGSG (SEQ ID NO: 67),

A98ATGTG (SEQ ID NO: 68),

A98GI+S99H+G100S+S101A, or

A98GP+S99A.

86. The modified subtilase of claim 76, comprising at least one further mutation at one or more positions.

87. The modified subtilase of claim 86, wherein the one or more positions are selected from the group consisting of: 27, 36, 57, 76, 97, 101, 104, 120, 123, 167, 170, 206, 218, 222, 224, 235 and 274.

88. The modified subtilase of claim 87, wherein the at least one further mutation is selected from the group consisting of K27R, *36D, S57P, N76D, S87N, G97N, S101G, V104A, V104N, V104Y, H120D, N123S, Y167X, R170X, Q206E, N218S, M222A, M222S, T224S, K235L, and T274A.

89. The modified subtilase of claim 88, wherein the at least one further mutation is selected from the group consisting of K27R+V104Y+N123S+T274A, N76D+S103A+V104I, N76D+V104A, S87N+S101G+V104N, S101G+V104N, and any other combination of K27R, N76D, S101G, V104A, V104N, V104Y, N123S, and T274A.

90. The modified subtilase of claim 86, wherein the one or more positions are selected from the group consisting of 129, 131, 133 and 194.

91. The modified subtilase of claim 90, wherein the at least one further mutation is selected from the group consisting of P129K, P131H, A133D, A133P, and A194P.

92. The modified subtilase of claim 76, wherein the subtilase is a subtilase of sub-group I-S1.

93. The modified subtilase of claim 92, wherein the subtilase is selected from the group consisting of subtilisin I168, subtilisin BPN', subtilisin DY, and subtilisin Carlsberg.

94. The modified subtilase of claim 76, wherein the subtilase is a subtilase of sub-group I-S2.

95. The modified subtilase of claim 94, wherein the subtilase is selected from the group consisting of subtilisin 147, subtilisin 309, subtilisin PB92, and subtilisin YaB.

96. A composition comprising a modified subtilase of claim 76 and a surfactant.

97. The composition of claim 96, which further comprises an amylase, cellulase, cutinase, lipase, oxidoreductase, or another protease.

98. A DNA sequence encoding a modified subtilase of claim 76.

99. A vector comprising a DNA sequence of claim 98.

100. A microbial host cell transformed with a vector of claim 99.

101. A method for producing a modified subtilase, comprising
    (a) culturing a microbial host cell of claim 100 under conditions conducive to the expression and secretion of the modified subtilase, and
    (b) recovering the modified subtilase.

102. A modified subtilase comprising a mutation in an amino acid sequence of a subtilase, wherein the mutation is an insertion of one or more amino acid residues at position 99 of the active site loop (b) region corresponding to positions 95 to 103, wherein the positions are numbered according to the amino acid sequence of the mature subtilisin BPN' of SEQ ID NO: 4.

103. The modified subtilase of claim 102, wherein the one or more amino acid residues are A, G, S, or T.

104. The modified subtilase of claim 102, wherein the one or more amino acid residues are D, E, H, K, or R.

105. The modified subtilase of claim 102, wherein the one or more amino acid residues are C, N, Q, S or T.

106. The modified subtilase of claim 102, wherein the one or more amino acid residues are A, G or V.

107. The modified subtilase of claim 102, wherein the one or more amino acid residues are F, I, L, M, P, W or Y.

108. The modified subtilase of claim 98, wherein the mutation comprises: S99SA, S99SC, S99SD, S99SE, S99SF, S99SG, S99SH, S99SI, S99SK, S99SL, S99SM, S99SN, S99SP, S99SQ, S99SR, S99SS, S99ST, S99SV, S99SW, or S99SY.

109. The modified subtilase of claim 102, wherein the mutation is an insertion of two or more amino acid residues at position 99.

110. The modified subtilase of claim 102, comprising:
    A98G+S99SQ,
    S99ASG+S101T,
    S99SA, S99SG,
    S99TC+S101C,
    S99TG+S101G,
    S99TK,
    S99TN,
    S99TP,
    S99TQ, or
    S99TR.

111. The modified subtilase of claim 102, comprising at least one further mutation at one or more positions.

112. The modified subtilase of claim 102, wherein the one or more positions are selected from the group consisting of: 27, 36, 57, 76, 87, 97, 101, 104, 120, 123, 167, 170, 206, 218, 222, 224, 235 and 274.

113. The modified subtilase of claim 112, wherein the at least one further mutation is selected from the group consisting of K27R, *36D, S57P, N76D, S87N, G97N, S101G, V104A, V104N, V104Y, H120D, N123S, Y167X, R170X, Q206E, N218S, M222A, M222S, T224S, K235L, and T274A.

114. The modified subtilase of claim 113, wherein the one at least one further mutation is selected from the group consisting of K27R+V104Y+N123S+T274A, N76D+S103A+V104I, N76D+V104A, S87N+S101G+V104N, S101G+V104N, and any other combination of K27R, N76D, S101G, V104A, V104N, V104Y, N123S, and T274A.

115. The modified subtilase of claim 102, comprising at least one further mutation at one or more other positions selected from the group consisting of 129, 131, 133 and 194.

116. The modified subtilase of claim 115, wherein the one at least one further mutation is selected from the group consisting of P129K, P131H, A133D, A133P, and A194P.

117. The modified subtilase of claim 102, wherein the subtilase is a subtilase of sub-group I-S1.

118. The modified subtilase of claim 117, wherein the subtilase is selected from the group consisting of subtilisin I168, subtilisin BPN', subtilisin DY, and subtilisin Carlsberg.

119. The modified subtilase of claim 102, wherein the subtilase is a subtilase of sub-group I-S2.

120. The modified subtilase of claim 117, wherein the subtilase is selected from the group consisting of subtilisin 147, subtilisin 309, subtilisin PB92, and subtilisin YaB.

121. A composition comprising a modified subtilase of claim 102 and a surfactant.

122. The composition of claim 121, which additionally comprises an amylase, cellulase, cutinase, oxidoreductase, lipase, or another protease.

123. A DNA sequence encoding a modified subtilase of claim 102.

124. An expression vector comprising a DNA sequence of claim 123.

125. A microbial host cell transformed with an expression vector of claim 124.

126. A method for producing a modified subtilase, comprising
    (a) culturing a microbial host cell of claim 125 under conditions conducive to the expression and secretion of the modified subtilase, and
    (b) recovering the modified subtilase.

127. A modified subtilase comprising a mutation in an amino acid sequence of a subtilase, wherein the mutation is an insertion of one or more amino acid residues at position 100 of the active site loop (b) region corresponding to positions 95 to 103, wherein the positions are numbered according to the amino acid sequence of the mature subtilisin BPN' of SEQ ID NO: 4.

128. The modified subtilase of claim 127, wherein the one or more amino acid residues are A, G, S, or T.

129. The modified subtilase of claim 127, wherein the one or more amino acid residues are D, E, H, K, or R.

130. The modified subtilase of claim 127, wherein the one or more amino acid residues are C, N, Q, S or T.

131. The modified subtilase of claim 127, wherein the one or more amino acid residues are A, G or V.

132. The modified subtilase of claim 127, wherein the one or more amino acid residues are F, I, L, M, P, W or Y.

133. The modified subtilase of claim 122, wherein the mutation comprises: G100GA, G100GC, G100GD, G100GE, G100GF, G100GG, G100GH, G100GI, G100GK, G100GL, G100GM, G100GN, G100GP, G100GQ, G100GR, G100GS, G100GT, G100GV, G100GW, or G100GY.

134. The modified subtilase of claim 127, wherein the mutation is an insertion of two or more amino acid residues at position 100.

135. The modified subtilase of claim 127, comprising A98G+G100GA+S101A+S103T or S99G+G100GGT+S101T.

136. The modified subtilase of claim 135, comprising at least one further mutation at one or more positions.

137. The modified subtilase of claim 136, wherein the one or more positions are selected from the group consisting of: 27, 36, 57, 76, 87, 97, 101, 104, 120, 123, 167, 170, 206, 218, 222, 224, 235 and 274.

138. The modified subtilase of claim 137, wherein the at least one further mutation is selected from the group consisting of K27R, *36D, S57P, N76D, S87N, G97N, S101G, V104A, V104N, V104Y, H120D, N123S, Y167X, R170X, Q206E, N218S, M222A, M222S, T224S, K235L, and T274A.

139. The modified subtilase of claim 138, wherein the at least one further mutation is selected from the group consisting of K27R+V104Y+N123S+T274A, N76D+S103A+V104I, N76D+V104A, S87N+S101G+V104N, S101G+V104N, and any other combination of K27R, N76D, S101G, V104A, V104N, V104Y, N123S, and T274A.

140. The modified subtilase of claim 136, wherein the one or more positions are selected from the group consisting of 129, 131, 133 and 194.

141. The modified subtilase of claim 140, wherein the at least one further mutation is selected from the group consisting of P129K, P131H, A133D, A133P, and A194P.

142. The modified subtilase of claim 127, wherein the subtilase is a subtilase of sub-group I-S1.

143. The modified subtilase of claim 142, wherein the subtilase is selected from the group consisting of subtilisin I168, subtilisin BPN', subtilisin DY, and subtilisin Carlsberg.

144. The modified subtilase of claim 127, wherein the subtilase is a subtilase of sub-group I-S2.

145. The modified subtilase of claim 144, wherein the subtilase is selected from the group consisting of subtilisin 147, subtilisin 309, subtilisin PB92, and subtilisin YaB.

146. A composition comprising a modified subtilase of claim 127 and a surfactant.

147. The composition of claim 146, which additionally comprises an amylase, cellulase, cutinase, lipase, oxidoreductase, or another protease.

148. A DNA sequence encoding a modified subtilase of claim 127.

149. An expression vector comprising a DNA sequence of claim 148.

150. A microbial host cell transformed with an expression vector of claim 149.

151. A method for producing a modified subtilase, comprising (a) culturing a microbial host cell of claim 150 under conditions conducive to the expression and secretion of the modified subtilase, and (b) recovering the modified subtilase.

152. A modified subtilase comprising a mutation in an amino acid sequence of a subtilase, wherein the mutation is an insertion of one or more amino acid residues at position 101 of the active site loop (b) region corresponding to positions 95 to 103, wherein the positions are numbered according to the amino acid sequence of the mature subtilisin BPN' of SEQ ID NO: 4.

153. The modified subtilase of claim 152, wherein the one or more amino acid residues are A, G, S, or T.

154. The modified subtilase of claim 152, wherein the one or more amino acid residues are D, E, H, K, or R.

155. The modified subtilase of claim 152, wherein the one or more amino acid residues are C, N, Q, S or T.

156. The modified subtilase of claim 152, wherein the one or more amino acid residues are A, G or V.

157. The modified subtilase of claim 152, wherein the one or more amino acid residues are F, I, L, M, P, W or Y.

158. The modified subtilase of claim 146, wherein the mutation comprises: S101SA, S101SC, S101SD, S101SE, S101SF, S101SG, S101SH, S101SI, S101SK, S101SL, S101SM, S101SN, S101SP, S101SQ, S101SR, S101SS, S101ST, S101SV, S101SW, or S101SY.

159. The modified subtilase of claim 152, wherein the mutation is an insertion of two or more amino acid residues at position 101.

160. The modified subtilase of claim 152, comprising A98G+S101ST, A98G+S101SG+S103T, A98G+S99A+S101ST, or S101SGAA (SEQ ID NO: 69).

161. The modified subtilase of claim 152, comprising at least one further mutation at one or more positions.

162. The modified subtilase of claim 154, wherein the one or more positions are selected from the group consisting of: 27, 36, 57, 76, 87, 97, 104, 120, 123, 167, 170, 206, 218, 222, 224, 235 and 274.

163. The modified subtilase of claim 162, wherein the at least one further mutation is selected from the group consisting of K27R, *36D, S57P, N76D, S87N, G97N, V104A, V104N, V104Y, H120D, N123S, Y167X, R170X, Q206E, N218S, M222A, M222S, T224S, K235L, and T274A.

164. The modified subtilase of claim 163, wherein the at least one further mutation is selected from the group consisting of K27R+V104Y+N123S+T274A, N76D+S103A+V104I, N76D+V104A, S87N+S101G+V104N, S101G+V104N, and any other combination of K27R, N76D, S101G, V104A, V104N, V104Y, N123S, and T274A.

165. The modified subtilase of claim 161, wherein the one or more positions are selected from the group consisting of 129, 131, 133 and 194.

166. The modified subtilase of claim 165, wherein the at least one further mutation is selected from the group consisting of P129K, P131H, A133D, A133P, and A194P.

167. The modified subtilase of claim 152, wherein the subtilase is a subtilase of sub-group I-S1.

168. The modified subtilase of claim 167, wherein the subtilase is selected from the group consisting of subtilisin I168, subtilisin BPN', subtilisin DY, and subtilisin Carlsberg.

169. The modified subtilase of claim 152, wherein the subtilase is a subtilase of sub-group I-S2.

170. The modified subtilase of claim 169, wherein the subtilase is selected from the group consisting of subtilisin 147, subtilisin 309, subtilisin PB92, and subtilisin YaB.

171. A composition comprising a modified subtilase of claim 152 and a surfactant.

172. The composition of claim 152, which additionally comprises an amylase, cellulase, cutinase, lipase, oxidoreductase, or another protease.

173. A DNA sequence encoding a modified subtilase of claim 152.

174. An expression vector comprising a DNA sequence of claim 173.

175. A microbial host cell transformed with an expression vector of claim 174.

176. A method for producing a modified subtilase, comprising
(a) culturing a microbial host cell of claim 175 under conditions conducive to the expression and secretion of the modified subtilase, and
(b) recovering the modified subtilase.

177. A modified subtilase comprising a mutation in an amino acid sequence of a subtilase, wherein the mutation is an insertion of one or more amino acid residues at position 102 of the active site loop (b) region corresponding to positions 95 to 103, numbered according to the amino acid sequence of the mature subtilisin BPN' of SEQ ID NO: 4.

178. The modified subtilase of claim 177, wherein the one or more amino acid residues are A, G, S, or T.

179. The modified subtilase of claim 177, wherein the one or more amino acid residues are D, E, H, K, or R.

180. The modified subtilase of claim 177, wherein the one or more amino acid residues are C, N, Q, S or T.

181. The modified subtilase of claim 177, wherein the one or more amino acid residues are A, G or V.

182. The modified subtilase of claim 177, wherein the one or more amino acid residues are F, I, L, M, P, W or Y.

183. The modified subtilase of claim 170, wherein the mutation comprises: G102GA, G102GC, G102GD, G102GE, G102GF, G102GG, G102GH, G102GI, G102GK, G102GL, G102GM, G102GN, G102GP, G102GQ, G102GR, G102GS, G102GT, G102GV, G102GW, or G102GY.

184. The modified subtilase of claim 177, wherein the mutation is an insertion of two or more amino acid residues at position 102.

185. The modified subtilase of claim 177, comprising G102GT+Y167A.

186. The modified subtilase of claim 177, comprising at least one further mutation at one or more positions.

187. The modified subtilase of claim 186, wherein the one or more positions are selected from the group consisting of: 27, 36, 57, 76, 87, 97, 101, 104, 120, 123, 167, 170, 206, 218, 222, 224, 235 and 274.

188. The modified subtilase of claim 187, wherein the at least one further mutation is selected from the group consisting of K27R, *36D, S57P, N76D, S87N, G97N, S101G, V104A, V104N, V104Y, H120D, N123S, Y167X, R170X, Q206E, N218S, M222A, M222S, T224S, K235L, and T274A.

189. The modified subtilase of claim 188, wherein the at least one further mutation is selected from the group consisting of K27R+V104Y+N123S+T274A, N76D+S103A+ V104I, N76D+V104A, S87N+S101G+V104N, S101G+ V104N, and any other combination of K27R, N76D, S101G, V104A, V104N, V104Y, N123S, and T274A.

190. The modified subtilase of claim 186, wherein the one or more positions are selected from the group consisting of 129, 131, 133 and 194.

191. The modified subtilase of claim 190, wherein the at least one further mutation is selected from the group consisting of P129K, P131H, A133D, A133P, and A194P.

192. The modified subtilase of claim 177, wherein the subtilase is a subtilase of sub-group I-S1.

193. The modified subtilase of claim 184, wherein the subtilase is selected from the group consisting of subtilisin I168, subtilisin BPN', subtilisin DY, and subtilisin Carlsberg.

194. The modified subtilase of claim 177, wherein the subtilase is a subtilase of sub-group I-S2.

195. The modified subtilase of claim 186, wherein the subtilase is selected from the group consisting of subtilisin 147, subtilisin 309, subtilisin PB92, and subtilisin YaB.

196. A composition comprising a modified subtilase of claim 177 and a surfactant.

197. The composition of claim 188, which additionally comprises a cellulase, lipase, cutinase, oxidoreductase, another protease, or an amylase.

198. A DNA sequence encoding a modified subtilase of claim 177.

199. An expression vector comprising a DNA sequence of claim 190.

200. A microbial host cell transformed with an expression vector of claim 191.

201. A method for producing a modified subtilase, comprising
(a) culturing a microbial host cell of claim 192 under conditions conducive to the expression and secretion of the modified subtilase, and
(b) recovering the modified subtilase.

202. A modified subtilase comprising a mutation in an amino acid sequence of a subtilase, wherein the mutation is an insertion of one or more amino acid residues at position 103 of the active site loop (b) region corresponding to positions 95 to 103, wherein the positions are numbered according to the amino acid sequence of the mature subtilisin BPN' of SEQ ID NO: 4.

203. The modified subtilase of claim 202, wherein the one or more amino acid residues are A, G, S, or T.

204. The modified subtilase of claim 202, wherein the one or more amino acid residues are D, E, H, K, or R.

205. The modified subtilase of claim 202, wherein the one or more amino acid residues are C, N, Q, S or T.

206. The modified subtilase of claim 202, wherein the one or more amino acid residues are A, G or V.

207. The modified subtilase of claim 202, wherein the one or more amino acid residues are F, I, L, M, P, W or Y.

208. The modified subtilase of claim 25, wherein the mutation comprises: S103SA, S103SC, S103SD, S103SE, S103SF, S103SH, S103SI, S103SK, S103SL, S103SM, S103SN, S103SP, S103SQ, S103SR, S103SS, S103ST, S103SV, S103SW, or S103SY.

209. The modified subtilase of claim 202, wherein the mutation is an insertion of two or more amino acid residues at position 103.

210. The modified subtilase of claim 202, comprising S103ST+Y167A.

211. The modified subtilase of claim 202, comprising at least one further mutation at one or more positions.

212. The modified subtilase of claim 211, wherein the one or more positions are selected from the group consisting of: 27, 36, 57, 76, 87, 97, 101, 104, 120, 123, 167, 170, 206, 218, 222, 224, 235 and 274.

213. The modified subtilase of claim 212, wherein the at least one further mutation is selected from the group consisting of K27R, *36D, S57P, N76D, S87N, G97N, S101G, V104A, V104N, V104Y, H120D, N123S, Y167X, R170X, Q206E, N218S, M222A, M222S, T224S, K235L, and T274A.

214. The modified subtilase of claim 213, wherein the at least one further mutation is selected from the group consisting of K27R+V104Y+N123S+T274A, N76D+S103A+V104I, N76D+V104A, S87N+S101G+V104N, S101G+V104N, and any other combination of K27R, N76D, S101G, V104A, V104N, V104Y, N123S, and T274A.

215. The modified subtilase of claim 211, wherein the one or more positions selected from the group consisting of 129, 131, 133 and 194.

216. The modified subtilase of claim 215, wherein the at least one further mutation is selected from the group consisting of P129K, P131H, A133D, A133P, and A194P.

217. The modified subtilase of claim 202, wherein the subtilase is a subtilase of sub-group I-S1.

218. The modified subtilase of claim 217, wherein the subtilase is selected from the group consisting of subtilisin I168, subtilisin BPN', subtilisin DY, and subtilisin Carlsberg.

219. The modified subtilase of claim 202, wherein the subtilase is a subtilase of sub-group I-S2.

220. The modified subtilase of claim 219, wherein the subtilase is selected from the group consisting of subtilisin 147, subtilisin 309, subtilisin PB92, and subtilisin YaB.

221. A composition comprising a modified subtilase of claim 202 and a surfactant.

222. The composition of claim 221, which additionally comprises an amylase, cellulase, cutinase, lipase, oxidoreductase, or another protease.

223. A DNA sequence encoding a modified subtilase of claim 202.

224. An expression vector comprising a DNA sequence of claim 223.

225. A microbial host cell transformed with an expression vector of claim 224.

226. A method for producing a modified subtilase, comprising (a) culturing a microbial host cell of claim 225 under conditions conducive to the expression and secretion of the modified subtilase, and (b) recovering the modified subtilase.

* * * * *

SEQUENCE LISTING

<160> NUMBER OF SEQ ID NOS: 69

<210> SEQ ID NO 1
<211> LENGTH: 3
<212> TYPE: PRT
<213> ORGANISM: Artificial Sequence
<220> FEATURE:
<223> OTHER INFORMATION: Synthetic

<400> SEQUENCE: 1

Ala Gly Leu
1

<210> SEQ ID NO 2
<211> LENGTH: 6
<212> TYPE: PRT
<213> ORGANISM: Artificial Sequence
<220> FEATURE:

<223> OTHER INFORMATION: Synthetic

<400> SEQUENCE: 2

Ala Gly Lys Ala Ser Leu
1               5

<210> SEQ ID NO 3
<211> LENGTH: 4
<212> TYPE: PRT
<213> ORGANISM: Artificial Sequence
<220> FEATURE:
<223> OTHER INFORMATION: Synthetic

<400> SEQUENCE: 3

Ala Gly Gly Leu
1

<210> SEQ ID NO 4
<211> LENGTH: 275
<212> TYPE: PRT
<213> ORGANISM: Bacillus

<400> SEQUENCE: 4

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
    130                 135                 140

Ser Gly Val Val Val Ala Ala Ala Gly Asn Glu Gly Thr Ser Gly Ser
145                 150                 155                 160

Ser Ser Thr Val Gly Tyr Pro Gly Lys Tyr Pro Ser Val Ile Ala Val
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
    210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

```
Ala Ala Gln
        275

<210> SEQ ID NO 5
<211> LENGTH: 269
<212> TYPE: PRT
<213> ORGANISM: Bacillus

<400> SEQUENCE: 5

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 6
<211> LENGTH: 274
<212> TYPE: PRT
<213> ORGANISM: Bacillus

<400> SEQUENCE: 6

Ala Gln Thr Val Pro Tyr Gly Ile Pro Leu Ile Lys Ala Asp Lys Val
1               5                   10                  15

Gln Ala Gln Gly Phe Lys Gly Ala Asn Val Lys Val Ala Val Leu Asp
            20                  25                  30

Thr Gly Ile Gln Ala Ser His Pro Asp Leu Asn Val Val Gly Gly Ala
        35                  40                  45
```

```
Ser Phe Val Ala Gly Glu Ala Tyr Asn Thr Asp Gly Asn Gly His Gly
 50                  55                  60

Thr His Val Ala Gly Thr Val Ala Ala Leu Asp Asn Thr Thr Gly Val
 65                  70                  75                  80

Leu Gly Val Ala Pro Ser Val Ser Leu Tyr Ala Val Lys Val Leu Asn
                 85                  90                  95

Ser Ser Gly Ser Gly Thr Tyr Ser Gly Ile Val Ser Gly Ile Glu Trp
            100                 105                 110

Ala Thr Thr Asn Gly Met Asp Val Ile Asn Met Ser Leu Gly Gly Pro
                115                 120                 125

Ser Gly Ser Thr Ala Met Lys Gln Ala Val Asp Asn Ala Tyr Ala Arg
130                 135                 140

Gly Val Val Val Ala Ala Ala Gly Asn Ser Gly Ser Ser Gly Asn
145                 150                 155                 160

Thr Asn Thr Ile Gly Tyr Pro Ala Lys Tyr Asp Ser Val Ile Ala Val
                165                 170                 175

Gly Ala Val Asp Ser Asn Ser Asn Arg Ala Ser Phe Ser Ser Val Gly
                180                 185                 190

Ala Glu Leu Glu Val Met Ala Pro Gly Ala Gly Val Tyr Ser Thr Tyr
                195                 200                 205

Pro Thr Ser Thr Tyr Ala Thr Leu Asn Gly Thr Ser Met Ala Ser Pro
210                 215                 220

His Val Ala Gly Ala Ala Ala Leu Ile Leu Ser Lys His Pro Asn Leu
225                 230                 235                 240

Ser Ala Ser Gln Val Arg Asn Arg Leu Ser Ser Thr Ala Thr Tyr Leu
                245                 250                 255

Gly Ser Ser Phe Tyr Tyr Gly Lys Gly Leu Ile Asn Val Glu Ala Ala
                260                 265                 270

Ala Gln

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
ctaaatattc gtggtggcgc                                            20

<210> SEQ ID NO 8
<211> LENGTH: 24
<212> TYPE: DNA
<213> ORGANISM: Artificial Sequence
<220> FEATURE:
<223> OTHER INFORMATION: Primer

<400> SEQUENCE: 8
gactttaaca gcgtatagct cagc                                       24

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
ctaaatattc gtggtggcgc                                            20
```

```
<210> SEQ ID NO 10
<211> LENGTH: 24
<212> TYPE: DNA
<213> ORGANISM: Artificial Sequence
<220> FEATURE:
<223> OTHER INFORMATION: Primer

<400> SEQUENCE: 10
gactttaaca gcgtatagct cagc                                          24

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
ctaaatattc gtggtggcgc                                               20

<210> SEQ ID NO 12
<211> LENGTH: 24
<212> TYPE: DNA
<213> ORGANISM: Artificial Sequence
<220> FEATURE:
<223> OTHER INFORMATION: Primer

<400> SEQUENCE: 12
gactttaaca gcgtatagct cagc                                          24

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
ctaaatattc gtggtggcgc                                               20

<210> SEQ ID NO 14
<211> LENGTH: 24
<212> TYPE: DNA
<213> ORGANISM: Artificial Sequence
<220> FEATURE:
<223> OTHER INFORMATION: Primer

<400> SEQUENCE: 14
gactttaaca gcgtatagct cagc                                          24

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
ctaaatattc gtggtggcgc                                               20

<210> SEQ ID NO 16
<211> LENGTH: 24
<212> TYPE: DNA
<213> ORGANISM: Artificial Sequence
<220> FEATURE:
```

-continued

```
<223> OTHER INFORMATION: Primer

<400> SEQUENCE: 16
gactttaaca gcgtatagct cagc                                           24

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
ctaaatattc gtggtggcgc                                                20

<210> SEQ ID NO 18
<211> LENGTH: 24
<212> TYPE: DNA
<213> ORGANISM: Artificial Sequence
<220> FEATURE:
<223> OTHER INFORMATION: Primer

<400> SEQUENCE: 18
gactttaaca gcgtatagct cagc                                           24

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
ctaaatattc gtggtggcgc                                                20

<210> SEQ ID NO 20
<211> LENGTH: 24
<212> TYPE: DNA
<213> ORGANISM: Artificial Sequence
<220> FEATURE:
<223> OTHER INFORMATION: Primer

<400> SEQUENCE: 20
gactttaaca gcgtatagct cagc                                           24

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
ctaaatattc gtggtggcgc                                                20

<210> SEQ ID NO 22
<211> LENGTH: 24
<212> TYPE: DNA
<213> ORGANISM: Artificial Sequence
<220> FEATURE:
<223> OTHER INFORMATION: Primer

<400> SEQUENCE: 22
gactttaaca gcgtatagct cagc                                           24
```

```
<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
ctaaatattc gtggtggcgc                                                 20

<210> SEQ ID NO 24
<211> LENGTH: 24
<212> TYPE: DNA
<213> ORGANISM: Artificial Sequence
<220> FEATURE:
<223> OTHER INFORMATION: Primer

<400> SEQUENCE: 24
gactttaaca gcgtatagct cagc                                            24

<210> SEQ ID NO 25
<211> LENGTH: 50
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (25)..(25)
OTHER INFORMATION: n denotes any nucleotide
<220> FEATURE:
<221> NAME/KEY: misc_feature
<222> LOCATION: (26)..(26)
<223> OTHER INFORMATION: n denotes any nucleotide

<400> SEQUENCE: 25
gctgagctat acgctgttaa agtcnnscta ggggcgagcg gttcaggttc                 50

<210> SEQ ID NO 26
<211> LENGTH: 21
<212> TYPE: DNA
<213> ORGANISM: Artificial Sequence
<220> FEATURE:
<223> OTHER INFORMATION: Primer

<400> SEQUENCE: 26
ccctttaacc gcacagcgtt t                                               21

<210> SEQ ID NO 27
<211> LENGTH: 50
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (28)..(28)
<223> OTHER INFORMATION: n denotes any nucleotide
<220> FEATURE:
<221> NAME/KEY: misc_feature
<222> LOCATION: (29)..(29)
<223> OTHER INFORMATION: n denotes any nucleotide

<400> SEQUENCE: 27
gctgagctat acgctgttaa agtcctanns ggggcgagcg gttcaggttc                 50

<210> SEQ ID NO 28
<211> LENGTH: 21
<212> TYPE: DNA
```

```
<213> ORGANISM: Artificial Sequence
<220> FEATURE:
<223> OTHER INFORMATION: Primer

<400> SEQUENCE: 28
ccctttaacc gcacagcgtt t                                               21

<210> SEQ ID NO 29
<211> LENGTH: 50
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (31)..(31)
OTHER INFORMATION: n denotes any nucleotide
<220> FEATURE:
<221> NAME/KEY: misc_feature
<222> LOCATION: (32)..(32)
<223> OTHER INFORMATION: n denotes any nucleotide

<400> SEQUENCE: 29
gctgagctat acgctgttaa agtcctaggg nnsgcgagcg gttcaggttc                 50

<210> SEQ ID NO 30
<211> LENGTH: 21
<212> TYPE: DNA
<213> ORGANISM: Artificial Sequence
<220> FEATURE:
<223> OTHER INFORMATION: Primer

<400> SEQUENCE: 30
ccctttaacc gcacagcgtt t                                               21

<210> SEQ ID NO 31
<211> LENGTH: 57
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (34)..(34)
<223> OTHER INFORMATION: n denotes any nucleotide
<220> FEATURE:
<221> NAME/KEY: misc_feature
<222> LOCATION: (35)..(35)
<223> OTHER INFORMATION: n denotes any nucleotide

<400> SEQUENCE: 31
gctgagctat acgctgttaa agtcctaggg gcgnnsagcg gttcaggttc ggtcagc         57

<210> SEQ ID NO 32
<211> LENGTH: 21
<212> TYPE: DNA
<213> ORGANISM: Artificial Sequence
<220> FEATURE:
<223> OTHER INFORMATION: Primer

<400> SEQUENCE: 32
ccctttaacc gcacagcgtt t                                               21

<210> SEQ ID NO 33
<211> LENGTH: 45
<212> TYPE: DNA
<213> ORGANISM: Artificial Sequence
<220> FEATURE:
<223> OTHER INFORMATION: Primer
```

```
<220> FEATURE:
<221> NAME/KEY: misc_feature
<222> LOCATION: (22)..(22)
<223> OTHER INFORMATION: n denotes any nucleotide
<220> FEATURE:
<221> NAME/KEY: misc_feature
<222> LOCATION: (23)..(23)
<223> OTHER INFORMATION: n denotes any nucleotide

<400> SEQUENCE: 33
gttaaagtcc tagggcgag cnnsggttca ggttcggtca gctcg         45

<210> SEQ ID NO 34
<211> LENGTH: 21
<212> TYPE: DNA
<213> ORGANISM: Artificial Sequence
<220> FEATURE:
<223> OTHER INFORMATION: Primer

<400> SEQUENCE: 34
ccctttaacc gcacagcgtt t                                  21

<210> SEQ ID NO 35
<211> LENGTH: 49
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (25)..(25)
<223> OTHER INFORMATION: n denotes any nucleotides
<220> FEATURE:
<221> NAME/KEY: misc_feature
<222> LOCATION: (26)..(26)
<223> OTHER INFORMATION: n denotes any nucleotides

<400> SEQUENCE: 35
gttaaagtcc tagggcgag cggtnnstca ggttcggtca gctcgattg      49

<210> SEQ ID NO 36
<211> LENGTH: 21
<212> TYPE: DNA
<213> ORGANISM: Artificial Sequence
<220> FEATURE:
<223> OTHER INFORMATION: Primer

<400> SEQUENCE: 36
ccctttaacc gcacagcgtt t                                  21

<210> SEQ ID NO 37
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (22)..(22)
<223> OTHER INFORMATION: n denotes any nucleotide
<220> FEATURE:
<221> NAME/KEY: misc_feature
<222> LOCATION: (23)..(23)
<223> OTHER INFORMATION: n denotes any nucleotide

<400> SEQUENCE: 37
gtcctagggg cgagcggttc annsggttcg gtcagctcga ttgcc        45

<210> SEQ ID NO 38
```

-continued

```
<211> LENGTH: 21
<212> TYPE: DNA
<213> ORGANISM: Artificial Sequence
<220> FEATURE:
<223> OTHER INFORMATION: Primer

<400> SEQUENCE: 38
ccctttaacc gcacagcgtt t                                              21

<210> SEQ ID NO 39
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (22)..(22)
<223> OTHER INFORMATION: n denotes any nucleotide
<220> FEATURE:
<221> NAME/KEY: misc_feature
<222> LOCATION: (23)..(23)
<223> OTHER INFORMATION: n denotes any nucleotide

<400> SEQUENCE: 39 ctagggcga gcggttcagg tnnstcggtc agctcgattg cccaag                    46

<210> SEQ ID NO 40
<211> LENGTH: 21
<212> TYPE: DNA
<213> ORGANISM: Artificial Sequence
<220> FEATURE:
<223> OTHER INFORMATION: Primer

<400> SEQUENCE: 40
ccctttaacc gcacagcgtt t                                              21

<210> SEQ ID NO 41
<211> LENGTH: 51
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (25)..(25)
<223> OTHER INFORMATION: n denotes any nucleotide
<220> FEATURE:
<221> NAME/KEY: misc_feature
<222> LOCATION: (26)..(26)
<223> OTHER INFORMATION: n denotes any nucleotide

<400> SEQUENCE: 41 ctagggcga gcggttcagg ttcgnnsgtc agctcgattg cccaaggatt g              51

<210> SEQ ID NO 42
<211> LENGTH: 21
<212> TYPE: DNA
<213> ORGANISM: Artificial Sequence
<220> FEATURE:
<223> OTHER INFORMATION: Primer

<400> SEQUENCE: 42
ccctttaacc gcacagcgtt t                                              21

<210> SEQ ID NO 43
<211> LENGTH: 276
<212> TYPE: PRT
<213> ORGANISM: Artificial Sequence
```

```
<220> FEATURE:
<223> OTHER INFORMATION: Synthetic
<220> FEATURE:
<221> NAME/KEY: misc_feature
<222> LOCATION: (96)..(96)
<223> OTHER INFORMATION: Xaa denotes any amino acid

<400> SEQUENCE: 43

Ala Gln Thr Val Pro Tyr Gly Ile Pro Leu Ile Lys Ala Asp Lys Val
1               5                   10                  15

Gln Ala Gln Gly Phe Lys Gly Ala Asn Val Lys Val Ala Val Leu Asp
            20                  25                  30

Thr Gly Ile Gln Ala Ser His Pro Asp Leu Asn Val Gly Gly Ala
        35                  40                  45

Ser Phe Val Ala Gly Glu Ala Tyr Asn Thr Asp Gly Asn Gly His Gly
    50                  55                  60

Thr His Val Ala Gly Thr Val Ala Ala Leu Asp Asn Thr Thr Gly Val
65                  70                  75                  80

Leu Gly Val Ala Pro Ser Val Ser Leu Ala Tyr Ala Val Lys Val Xaa
                85                  90                  95

Leu Asn Ser Ser Gly Ser Gly Thr Tyr Ser Gly Ile Val Ser Gly Ile
                100                 105                 110

Glu Trp Ala Thr Thr Asn Gly Met Asp Val Ile Asn Met Ser Leu Gly
            115                 120                 125

Gly Pro Ser Gly Ser Thr Ala Met Lys Gln Ala Val Asp Asn Ala Tyr
        130                 135                 140

Ala Arg Gly Val Val Val Ala Ala Ala Gly Asn Ser Gly Ser Ser
145                 150                 155                 160

Gly Asn Thr Asn Thr Ile Gly Tyr Pro Ala Lys Tyr Asp Ser Val Ile
                165                 170                 175

Ala Val Gly Ala Val Asp Ser Asn Ser Asn Arg Ala Ser Phe Ser Ser
            180                 185                 190

Val Gly Ala Glu Leu Glu Val Met Ala Pro Gly Ala Gly Val Tyr Ser
        195                 200                 205

Thr Tyr Pro Thr Ser Thr Tyr Ala Thr Leu Asn Gly Thr Ser Met Ala
    210                 215                 220

Ser Pro His Val Ala Gly Ala Ala Ala Leu Ile Leu Ser Lys His Pro
225                 230                 235                 240

Asn Leu Ser Ala Ser Gln Val Arg Asn Arg Leu Ser Ser Thr Ala Thr
                245                 250                 255

Tyr Leu Gly Ser Ser Phe Tyr Tyr Gly Lys Gly Leu Ile Asn Val Glu
                260                 265                 270

Ala Ala Ala Gln
        275

<210> SEQ ID NO 44
<211> LENGTH: 271
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (95)..(95)
<223> OTHER INFORMATION: Xaa denotes any amino acid

<400> SEQUENCE: 44

Ala Gln Ser Val Pro Trp Gly Ile Ser Arg Val Gln Ala Pro Ala Ala
1               5                   10                  15
```

-continued

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
     50                  55                  60

His Val Ala Gly Thr Ile Ala Ala Leu Asn Asn Ser Ile Gly Val Leu
 65                  70                  75                  80

Gly Val Ala Pro Ser Ala Glu Leu Ala Tyr Ala Val Lys Val Xaa Leu
                 85                  90                  95

Gly Ala Ser Gly Ser Gly Ser Val Ser Ser Ile Ala Gln Gly Leu Glu
                100                 105                 110

Trp Ala Gly Asn Asn Gly Met His Val Ala Asn Leu Ser Leu Gly Ser
                115                 120                 125

Pro Ser Pro Ser Ala Thr Leu Glu Gln Ala Val Asn Ser Ala Thr Ser
            130                 135                 140

Arg Gly Val Leu Val Val Ala Ala Ser Gly Asn Ser Gly Ala Gly Ser
145                 150                 155                 160

Ile Ser Tyr Pro Ala Arg Tyr Ala Asn Ala Met Ala Val Gly Ala Thr
                165                 170                 175

Asp Gln Asn Asn Asn Arg Ala Ser Phe Ser Gln Tyr Gly Ala Gly Leu
            180                 185                 190

Asp Ile Val Ala Pro Gly Val Asn Val Gln Ser Thr Tyr Pro Gly Ser
            195                 200                 205

Thr Tyr Ala Ser Leu Asn Gly Thr Ser Met Ala Thr Pro His Val Ala
    210                 215                 220

Gly Ala Ala Ala Leu Val Lys Gln Lys Asn Pro Ser Trp Ser Asn Val
225                 230                 235                 240

Gln Ile Arg Asn His Leu Lys Asn Thr Ala Thr Ser Leu Gly Ser Thr
                245                 250                 255

Asn Leu Tyr Gly Ser Gly Leu Val Asn Ala Glu Ala Ala Thr Arg
                260                 265                 270

<210> SEQ ID NO 45
<211> LENGTH: 276
<212> TYPE: PRT
<213> ORGANISM: Artificial Sequence
<220> FEATURE:
<223> OTHER INFORMATION: Syntehtic
<220> FEATURE:
<221> NAME/KEY: misc_feature
<222> LOCATION: (97)..(97)
<223> OTHER INFORMATION: Xaa denotes any amino acid

<400> SEQUENCE: 45

Ala Gln Thr Val Pro Tyr Gly Ile Pro Leu Ile Lys Ala Asp Lys Val
 1               5                  10                  15

Gln Ala Gln Gly Phe Lys Gly Ala Asn Val Lys Val Ala Val Leu Asp
                20                  25                  30

Thr Gly Ile Gln Ala Ser His Pro Asp Leu Asn Val Gly Gly Ala
            35                  40                  45

Ser Phe Val Ala Gly Glu Ala Tyr Asn Thr Asp Gly Asn Gly His Gly
 50                  55                  60

Thr His Val Ala Gly Thr Val Ala Ala Leu Asp Asn Thr Thr Gly Val
 65                  70                  75                  80

Leu Gly Val Ala Pro Ser Val Ser Leu Ala Tyr Ala Val Lys Val Leu

-continued

```
                85                  90                  95
Xaa Asn Ser Ser Gly Ser Gly Thr Tyr Ser Gly Ile Val Ser Gly Ile
            100                 105                 110
Glu Trp Ala Thr Thr Asn Gly Met Asp Val Ile Asn Met Ser Leu Gly
            115                 120                 125
Gly Pro Ser Gly Ser Thr Ala Met Lys Gln Ala Val Asp Asn Ala Tyr
            130                 135                 140
Ala Arg Gly Val Val Val Ala Ala Gly Asn Ser Gly Ser Ser
145                 150                 155                 160
Gly Asn Thr Asn Thr Ile Gly Tyr Pro Ala Lys Tyr Asp Ser Val Ile
                165                 170                 175
Ala Val Gly Ala Val Asp Ser Asn Ser Asn Arg Ala Ser Phe Ser Ser
            180                 185                 190
Val Gly Ala Glu Leu Glu Val Met Ala Pro Gly Ala Gly Val Tyr Ser
            195                 200                 205
Thr Tyr Pro Thr Ser Thr Tyr Ala Thr Leu Asn Gly Thr Ser Met Ala
            210                 215                 220
Ser Pro His Val Ala Gly Ala Ala Ala Leu Ile Leu Ser Lys His Pro
225                 230                 235                 240
Asn Leu Ser Ala Ser Gln Val Arg Asn Arg Leu Ser Ser Thr Ala Thr
                245                 250                 255
Tyr Leu Gly Ser Ser Phe Tyr Tyr Gly Lys Gly Leu Ile Asn Val Glu
                260                 265                 270
Ala Ala Ala Gln
        275

<210> SEQ ID NO 46
<211> LENGTH: 271
<212> TYPE: PRT
<213> ORGANISM: Artificial Sequence
<220> FEATURE:
<223> OTHER INFORMATION: Synthetic
<220> FEATURE:
<221> NAME/KEY: Misc_feature
<222> LOCATION: (96)..(96)
<223> OTHER INFORMATION: Xaa denotes any amino acid

<400> SEQUENCE: 46

Ala Gln Ser Val Pro Trp Gly Ile Ser Arg Val Gln Ala Pro Ala Ala
1               5                   10                  15
His Asn Arg Gly Leu Thr Gly Ser Gly Val Lys Val Ala Val Leu Asp
            20                  25                  30
Thr Gly Ile Ser Thr His Pro Asp Leu Asn Ile Arg Gly Gly Ala Ser
            35                  40                  45
Phe Val Pro Gly Glu Pro Ser Thr Gln Asp Gly Asn Gly His Gly Thr
        50                  55                  60
His Val Ala Gly Thr Ile Ala Ala Leu Asn Asn Ser Ile Gly Val Leu
65                  70                  75                  80
Gly Val Ala Pro Ser Ala Glu Leu Ala Tyr Ala Val Lys Val Leu Xaa
                85                  90                  95
Gly Ala Ser Gly Ser Gly Ser Val Ser Ser Ile Ala Gln Gly Leu Glu
            100                 105                 110
Trp Ala Gly Asn Asn Gly Met His Val Ala Asn Leu Ser Leu Gly Ser
            115                 120                 125
Pro Ser Pro Ser Ala Thr Leu Glu Gln Ala Val Asn Ser Ala Thr Ser
            130                 135                 140
```

```
Arg Gly Val Leu Val Ala Ala Ser Gly Asn Ser Gly Ala Gly Ser
145                 150                 155                 160

Ile Ser Tyr Pro Ala Arg Tyr Ala Asn Ala Met Ala Val Gly Ala Thr
            165                 170                 175

Asp Gln Asn Asn Asn Arg Ala Ser Phe Ser Gln Tyr Gly Ala Gly Leu
            180                 185                 190

Asp Ile Val Ala Pro Gly Val Asn Val Gln Ser Thr Tyr Pro Gly Ser
            195                 200                 205

Thr Tyr Ala Ser Leu Asn Gly Thr Ser Met Ala Thr Pro His Val Ala
            210                 215                 220

Gly Ala Ala Ala Leu Val Lys Gln Lys Asn Pro Ser Trp Ser Asn Val
225                 230                 235                 240

Gln Ile Arg Asn His Leu Lys Asn Thr Ala Thr Ser Leu Gly Ser Thr
            245                 250                 255

Asn Leu Tyr Gly Ser Gly Leu Val Asn Ala Glu Ala Ala Thr Arg
            260                 265                 270

<210> SEQ ID NO 47
<211> LENGTH: 276
<212> TYPE: PRT
<213> ORGANISM: Artificial Sequence
<220> FEATURE:
<223> OTHER INFORMATION: Synthetic
<220> FEATURE:
<221> NAME/KEY: Misc_feature
<222> LOCATION: (98)..(98)
<223> OTHER INFORMATION: Xaa denotes any amino acid

<400> SEQUENCE: 47

Ala Gln Thr Val Pro Tyr Gly Ile Pro Leu Ile Lys Ala Asp Lys Val
1               5                   10                  15

Gln Ala Gln Gly Phe Lys Gly Ala Asn Val Lys Val Ala Val Leu Asp
            20                  25                  30

Thr Gly Ile Gln Ala Ser His Pro Asp Leu Asn Val Gly Gly Ala
            35                  40                  45

Ser Phe Val Ala Gly Glu Ala Tyr Asn Thr Asp Gly Asn Gly His Gly
50                  55                  60

Thr His Val Ala Gly Thr Val Ala Ala Leu Asp Asn Thr Thr Gly Val
65                  70                  75                  80

Leu Gly Val Ala Pro Ser Val Ser Leu Ala Tyr Ala Val Lys Val Leu
                85                  90                  95

Asn Xaa Ser Ser Gly Ser Gly Thr Tyr Ser Gly Ile Val Ser Gly Ile
            100                 105                 110

Glu Trp Ala Thr Thr Asn Gly Met Asp Val Ile Asn Met Ser Leu Gly
            115                 120                 125

Gly Pro Ser Gly Ser Thr Ala Met Lys Gln Ala Val Asp Asn Ala Tyr
130                 135                 140

Ala Arg Gly Val Val Val Ala Ala Ala Gly Asn Ser Gly Ser Ser
145                 150                 155                 160

Gly Asn Thr Asn Thr Ile Gly Tyr Pro Ala Lys Tyr Asp Ser Val Ile
            165                 170                 175

Ala Val Gly Ala Val Asp Ser Asn Ser Asn Arg Ala Ser Phe Ser Ser
            180                 185                 190

Val Gly Ala Glu Leu Glu Val Met Ala Pro Gly Ala Gly Val Tyr Ser
            195                 200                 205

Thr Tyr Pro Thr Ser Thr Tyr Ala Thr Leu Asn Gly Thr Ser Met Ala
            210                 215                 220
```

```
Ser Pro His Val Ala Gly Ala Ala Leu Ile Leu Ser Lys His Pro
225                 230                 235                 240

Asn Leu Ser Ala Ser Gln Val Arg Asn Arg Leu Ser Ser Thr Ala Thr
            245                 250                 255

Tyr Leu Gly Ser Ser Phe Tyr Tyr Gly Lys Gly Leu Ile Asn Val Glu
            260                 265                 270

Ala Ala Ala Gln
        275

<210> SEQ ID NO 48
<211> LENGTH: 271
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (97)..(97)
<223> OTHER INFORMATION: Xaa denotes any amino acid

<400> SEQUENCE: 48

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Ala Tyr Ala Val Lys Val Leu Gly
                85                  90                  95

Xaa Ala Ser Gly Ser Gly Ser Val Ser Ser Ile Ala Gln Gly Leu Glu
            100                 105                 110

Trp Ala Gly Asn Asn Gly Met His Val Ala Asn Leu Ser Leu Gly Ser
        115                 120                 125

Pro Ser Pro Ser Ala Thr Leu Glu Gln Ala Val Asn Ser Ala Thr Ser
    130                 135                 140

Arg Gly Val Leu Val Val Ala Ala Ser Gly Asn Ser Gly Ala Gly Ser
145                 150                 155                 160

Ile Ser Tyr Pro Ala Arg Tyr Ala Asn Ala Met Ala Val Gly Ala Thr
                165                 170                 175

Asp Gln Asn Asn Asn Arg Ala Ser Phe Ser Gln Tyr Gly Ala Gly Leu
            180                 185                 190

Asp Ile Val Ala Pro Gly Val Asn Val Gln Ser Thr Tyr Pro Gly Ser
        195                 200                 205

Thr Tyr Ala Ser Leu Asn Gly Thr Ser Met Ala Thr Pro His Val Ala
    210                 215                 220

Gly Ala Ala Ala Leu Val Lys Gln Lys Asn Pro Ser Trp Ser Asn Val
225                 230                 235                 240

Gln Ile Arg Asn His Leu Lys Asn Thr Ala Thr Ser Leu Gly Ser Thr
                245                 250                 255

Asn Leu Tyr Gly Ser Gly Leu Val Asn Ala Glu Ala Ala Thr Arg
            260                 265                 270
```

-continued

```
<210> SEQ ID NO 49
<211> LENGTH: 276
<212> TYPE: PRT
<213> ORGANISM: Artificial Sequence
<220> FEATURE:
<223> OTHER INFORMATION: Synthetic
<220> FEATURE:
<221> NAME/KEY: Misc_feature
<222> LOCATION: (99)..(99)
<223> OTHER INFORMATION: Xaa denotes any amino acid

<400> SEQUENCE: 49

Ala Gln Thr Val Pro Tyr Gly Ile Pro Leu Ile Lys Ala Asp Lys Val
1               5                   10                  15

Gln Ala Gln Gly Phe Lys Gly Ala Asn Val Lys Val Ala Val Leu Asp
            20                  25                  30

Thr Gly Ile Gln Ala Ser His Pro Asp Leu Asn Val Gly Gly Ala
        35                  40                  45

Ser Phe Val Ala Gly Glu Ala Tyr Asn Thr Asp Gly Asn Gly His Gly
    50                  55                  60

Thr His Val Ala Gly Thr Val Ala Ala Leu Asp Asn Thr Thr Gly Val
65                  70                  75                  80

Leu Gly Val Ala Pro Ser Val Ser Leu Ala Tyr Ala Val Lys Val Leu
                85                  90                  95

Asn Ser Xaa Ser Gly Ser Gly Thr Tyr Ser Gly Ile Val Ser Gly Ile
            100                 105                 110

Glu Trp Ala Thr Thr Asn Gly Met Asp Val Ile Asn Met Ser Leu Gly
        115                 120                 125

Gly Pro Ser Gly Ser Thr Ala Met Lys Gln Ala Val Asp Asn Ala Tyr
    130                 135                 140

Ala Arg Gly Val Val Val Ala Ala Ala Gly Asn Ser Gly Ser Ser
145                 150                 155                 160

Gly Asn Thr Asn Thr Ile Gly Tyr Pro Ala Lys Tyr Asp Ser Val Ile
                165                 170                 175

Ala Val Gly Ala Val Asp Ser Asn Ser Asn Arg Ala Ser Phe Ser Ser
            180                 185                 190

Val Gly Ala Glu Leu Glu Val Met Ala Pro Gly Ala Gly Val Tyr Ser
        195                 200                 205

Thr Tyr Pro Thr Ser Thr Tyr Ala Thr Leu Asn Gly Thr Ser Met Ala
    210                 215                 220

Ser Pro His Val Ala Gly Ala Ala Ala Leu Ile Leu Ser Lys His Pro
225                 230                 235                 240

Asn Leu Ser Ala Ser Gln Val Arg Asn Arg Leu Ser Ser Thr Ala Thr
                245                 250                 255

Tyr Leu Gly Ser Ser Phe Tyr Tyr Gly Lys Gly Leu Ile Asn Val Glu
            260                 265                 270

Ala Ala Ala Gln
        275

<210> SEQ ID NO 50
<211> LENGTH: 271
<212> TYPE: PRT
<213> ORGANISM: Artificial Sequence
<220> FEATURE:
<223> OTHER INFORMATION: Synthetic
<220> FEATURE:
<221> NAME/KEY: Misc_feature
<222> LOCATION: (98)..(98)
<223> OTHER INFORMATION: Xaa denotes any amino acid
```

```
<400> SEQUENCE: 50

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Ala Tyr Ala Val Lys Val Leu Gly
                85                  90                  95

Ala Xaa Ser Gly Ser Gly Ser Val Ser Ser Ile Ala Gln Gly Leu Glu
            100                 105                 110

Trp Ala Gly Asn Asn Gly Met His Val Ala Asn Leu Ser Leu Gly Ser
            115                 120                 125

Pro Ser Pro Ser Ala Thr Leu Glu Gln Ala Val Asn Ser Ala Thr Ser
            130                 135                 140

Arg Gly Val Leu Val Val Ala Ala Ser Gly Asn Ser Gly Ala Gly Ser
145                 150                 155                 160

Ile Ser Tyr Pro Ala Arg Tyr Ala Asn Ala Met Ala Val Gly Ala Thr
                165                 170                 175

Asp Gln Asn Asn Asn Arg Ala Ser Phe Ser Gln Tyr Gly Ala Gly Leu
            180                 185                 190

Asp Ile Val Ala Pro Gly Val Asn Val Gln Ser Thr Tyr Pro Gly Ser
            195                 200                 205

Thr Tyr Ala Ser Leu Asn Gly Thr Ser Met Ala Thr Pro His Val Ala
        210                 215                 220

Gly Ala Ala Ala Leu Val Lys Gln Lys Asn Pro Ser Trp Ser Asn Val
225                 230                 235                 240

Gln Ile Arg Asn His Leu Lys Asn Thr Ala Thr Ser Leu Gly Ser Thr
                245                 250                 255

Asn Leu Tyr Gly Ser Gly Leu Val Asn Ala Glu Ala Ala Thr Arg
            260                 265                 270

<210> SEQ ID NO 51
<211> LENGTH: 276
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (100)..(100)
<223> OTHER INFORMATION: Xaa denotes any amino acid

<400> SEQUENCE: 51

Ala Gln Thr Val Pro Tyr Gly Ile Pro Leu Ile Lys Ala Asp Lys Val
1               5                   10                  15

Gln Ala Gln Gly Phe Lys Gly Ala Asn Val Lys Val Ala Val Leu Asp
            20                  25                  30

Thr Gly Ile Gln Ala Ser His Pro Asp Leu Asn Val Val Gly Gly Ala
        35                  40                  45

Ser Phe Val Ala Gly Glu Ala Tyr Asn Thr Asp Gly Asn Gly His Gly
    50                  55                  60
```

```
Thr His Val Ala Gly Thr Val Ala Ala Leu Asp Asn Thr Thr Gly Val
 65                  70                  75                  80

Leu Gly Val Ala Pro Ser Val Ser Leu Ala Tyr Ala Val Lys Val Leu
             85                  90                  95

Asn Ser Ser Xaa Gly Ser Gly Thr Tyr Ser Gly Ile Val Ser Gly Ile
            100                 105                 110

Glu Trp Ala Thr Thr Asn Gly Met Asp Val Ile Asn Met Ser Leu Gly
        115                 120                 125

Gly Pro Ser Gly Ser Thr Ala Met Lys Gln Ala Val Asp Asn Ala Tyr
    130                 135                 140

Ala Arg Gly Val Val Val Ala Ala Gly Asn Ser Gly Ser Ser
145                 150                 155                 160

Gly Asn Thr Asn Thr Ile Gly Tyr Pro Ala Lys Tyr Asp Ser Val Ile
                165                 170                 175

Ala Val Gly Ala Val Asp Ser Asn Ser Asn Arg Ala Ser Phe Ser Ser
            180                 185                 190

Val Gly Ala Glu Leu Glu Val Met Ala Pro Gly Ala Gly Val Tyr Ser
        195                 200                 205

Thr Tyr Pro Thr Ser Thr Tyr Ala Thr Leu Asn Gly Thr Ser Met Ala
    210                 215                 220

Ser Pro His Val Ala Gly Ala Ala Leu Ile Leu Ser Lys His Pro
225                 230                 235                 240

Asn Leu Ser Ala Ser Gln Val Arg Asn Arg Leu Ser Ser Thr Ala Thr
                245                 250                 255

Tyr Leu Gly Ser Ser Phe Tyr Tyr Gly Lys Gly Leu Ile Asn Val Glu
            260                 265                 270

Ala Ala Ala Gln
        275

<210> SEQ ID NO 52
<211> LENGTH: 271
<212> TYPE: PRT
<213> ORGANISM: Artificial Sequence
<220> FEATURE:
<223> OTHER INFORMATION: Synthetic
<220> FEATURE:
<221> NAME/KEY: Misc_feature
<222> LOCATION: (99)..(99)
<223> OTHER INFORMATION: Xaa denotes any amino acid

<400> SEQUENCE: 52

Ala Gln Ser Val Pro Trp Gly Ile Ser Arg Val Gln Ala Pro Ala Ala
  1               5                  10                  15

His Asn Arg Gly Leu Thr Gly Ser Gly Val Lys Val Ala Val Leu Asp
             20                  25                  30

Thr Gly Ile Ser Thr His Pro Asp Leu Asn Ile Arg Gly Gly Ala Ser
         35                  40                  45

Phe Val Pro Gly Glu Pro Ser Thr Gln Asp Gly Asn Gly His Gly Thr
     50                  55                  60

His Val Ala Gly Thr Ile Ala Ala Leu Asn Asn Ser Ile Gly Val Leu
 65                  70                  75                  80

Gly Val Ala Pro Ser Ala Glu Leu Ala Tyr Ala Val Lys Val Leu Gly
             85                  90                  95

Ala Ser Xaa Gly Ser Gly Ser Val Ser Ser Ile Ala Gln Gly Leu Glu
            100                 105                 110

Trp Ala Gly Asn Asn Gly Met His Val Ala Asn Leu Ser Leu Gly Ser
        115                 120                 125
```

-continued

```
Pro Ser Pro Ser Ala Thr Leu Glu Gln Ala Val Asn Ser Ala Thr Ser
        130                 135                 140

Arg Gly Val Leu Val Ala Ala Ser Gly Asn Ser Gly Ala Gly Ser
145                 150                 155                 160

Ile Ser Tyr Pro Ala Arg Tyr Ala Asn Ala Met Ala Val Gly Ala Thr
                165                 170                 175

Asp Gln Asn Asn Asn Arg Ala Ser Phe Ser Gln Tyr Gly Ala Gly Leu
            180                 185                 190

Asp Ile Val Ala Pro Gly Val Asn Val Gln Ser Thr Tyr Pro Gly Ser
        195                 200                 205

Thr Tyr Ala Ser Leu Asn Gly Thr Ser Met Ala Thr Pro His Val Ala
    210                 215                 220

Gly Ala Ala Ala Leu Val Lys Gln Lys Asn Pro Ser Trp Ser Asn Val
225                 230                 235                 240

Gln Ile Arg Asn His Leu Lys Asn Thr Ala Thr Ser Leu Gly Ser Thr
                245                 250                 255

Asn Leu Tyr Gly Ser Gly Leu Val Asn Ala Glu Ala Ala Thr Arg
            260                 265                 270

<210> SEQ ID NO 53
<211> LENGTH: 276
<212> TYPE: PRT
<213> ORGANISM: Artificial Sequence
<220> FEATURE:
<223> OTHER INFORMATION: Synthetic
<220> FEATURE:
<221> NAME/KEY: Misc_feature
<222> LOCATION: (101)..(101)
<223> OTHER INFORMATION: Xaa denotes any amino acid

<400> SEQUENCE: 53

Ala Gln Thr Val Pro Tyr Gly Ile Pro Leu Ile Lys Ala Asp Lys Val
1               5                   10                  15

Gln Ala Gln Gly Phe Lys Gly Ala Asn Val Lys Val Ala Val Leu Asp
            20                  25                  30

Thr Gly Ile Gln Ala Ser His Pro Asp Leu Asn Val Val Gly Gly Ala
        35                  40                  45

Ser Phe Val Ala Gly Glu Ala Tyr Asn Thr Asp Gly Asn Gly His Gly
    50                  55                  60

Thr His Val Ala Gly Thr Val Ala Ala Leu Asp Asn Thr Thr Gly Val
65                  70                  75                  80

Leu Gly Val Ala Pro Ser Val Ser Leu Ala Tyr Ala Val Lys Val Leu
                85                  90                  95

Asn Ser Ser Gly Xaa Ser Gly Thr Tyr Ser Gly Ile Val Ser Gly Ile
            100                 105                 110

Glu Trp Ala Thr Thr Asn Gly Met Asp Val Ile Asn Met Ser Leu Gly
        115                 120                 125

Gly Pro Ser Gly Ser Thr Ala Met Lys Gln Ala Val Asp Asn Ala Tyr
    130                 135                 140

Ala Arg Gly Val Val Val Ala Ala Ala Gly Asn Ser Gly Ser Ser
145                 150                 155                 160

Gly Asn Thr Asn Thr Ile Gly Tyr Pro Ala Lys Tyr Asp Ser Val Ile
                165                 170                 175

Ala Val Gly Ala Val Asp Ser Asn Ser Asn Arg Ala Ser Phe Ser Ser
            180                 185                 190

Val Gly Ala Glu Leu Glu Val Met Ala Pro Gly Ala Gly Val Tyr Ser
```

```
                    195                 200                 205
Thr Tyr Pro Thr Ser Thr Tyr Ala Thr Leu Asn Gly Thr Ser Met Ala
    210                 215                 220

Ser Pro His Val Ala Gly Ala Ala Leu Ile Leu Ser Lys His Pro
225                 230                 235                 240

Asn Leu Ser Ala Ser Gln Val Arg Asn Arg Leu Ser Ser Thr Ala Thr
                245                 250                 255

Tyr Leu Gly Ser Ser Phe Tyr Tyr Gly Lys Gly Leu Ile Asn Val Glu
            260                 265                 270

Ala Ala Ala Gln
        275

<210> SEQ ID NO 54
<211> LENGTH: 271
<212> TYPE: PRT
<213> ORGANISM: Artificial Sequence
<220> FEATURE:
<223> OTHER INFORMATION: Synthetic
<220> FEATURE:
<221> NAME/KEY: Misc_feature
<222> LOCATION: (100)..(100)
<223> OTHER INFORMATION: Xaa denotes any amino acid

<400> SEQUENCE: 54

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Ala Tyr Ala Val Lys Val Leu Gly
                85                  90                  95

Ala Ser Gly Xaa Ser Gly Ser Val Ser Ser Ile Ala Gln Gly Leu Glu
            100                 105                 110

Trp Ala Gly Asn Asn Gly Met His Val Ala Asn Leu Ser Leu Gly Ser
        115                 120                 125

Pro Ser Pro Ser Ala Thr Leu Glu Gln Ala Val Asn Ser Ala Thr Ser
    130                 135                 140

Arg Gly Val Leu Val Val Ala Ala Ser Gly Asn Ser Gly Ala Gly Ser
145                 150                 155                 160

Ile Ser Tyr Pro Ala Arg Tyr Ala Asn Ala Met Ala Val Gly Ala Thr
                165                 170                 175

Asp Gln Asn Asn Asn Arg Ala Ser Phe Ser Gln Tyr Gly Ala Gly Leu
            180                 185                 190

Asp Ile Val Ala Pro Gly Val Asn Val Gln Ser Thr Tyr Pro Gly Ser
        195                 200                 205

Thr Tyr Ala Ser Leu Asn Gly Thr Ser Met Ala Thr Pro His Val Ala
    210                 215                 220

Gly Ala Ala Ala Leu Val Lys Gln Lys Asn Pro Ser Trp Ser Asn Val
225                 230                 235                 240

Gln Ile Arg Asn His Leu Lys Asn Thr Ala Thr Ser Leu Gly Ser Thr
                245                 250                 255
```

```
Asn Leu Tyr Gly Ser Gly Leu Val Asn Ala Glu Ala Ala Thr Arg
            260                 265                 270

<210> SEQ ID NO 55
<211> LENGTH: 276
<212> TYPE: PRT
<213> ORGANISM: Artificial Sequence
<220> FEATURE:
<223> OTHER INFORMATION: Synthetic
<220> FEATURE:
<221> NAME/KEY: Misc_feature
<222> LOCATION: (102)..(102)
<223> OTHER INFORMATION: Xaa denotes any amino acid

<400> SEQUENCE: 55

Ala Gln Thr Val Pro Tyr Gly Ile Pro Leu Ile Lys Ala Asp Lys Val
1               5                   10                  15

Gln Ala Gln Gly Phe Lys Gly Ala Asn Val Lys Val Ala Val Leu Asp
            20                  25                  30

Thr Gly Ile Gln Ala Ser His Pro Asp Leu Asn Val Val Gly Gly Ala
        35                  40                  45

Ser Phe Val Ala Gly Glu Ala Tyr Asn Thr Asp Gly Asn Gly His Gly
    50                  55                  60

Thr His Val Ala Gly Thr Val Ala Ala Leu Asp Asn Thr Thr Gly Val
65                  70                  75                  80

Leu Gly Val Ala Pro Ser Val Ser Leu Ala Tyr Ala Val Lys Val Leu
                85                  90                  95

Asn Ser Ser Gly Ser Xaa Gly Thr Tyr Ser Gly Ile Val Ser Gly Ile
            100                 105                 110

Glu Trp Ala Thr Thr Asn Gly Met Asp Val Ile Asn Met Ser Leu Gly
        115                 120                 125

Gly Pro Ser Gly Ser Thr Ala Met Lys Gln Ala Val Asp Asn Ala Tyr
    130                 135                 140

Ala Arg Gly Val Val Val Ala Ala Ala Gly Asn Ser Gly Ser Ser Ser
145                 150                 155                 160

Gly Asn Thr Asn Thr Ile Gly Tyr Pro Ala Lys Tyr Asp Ser Val Ile
                165                 170                 175

Ala Val Gly Ala Val Asp Ser Asn Ser Asn Arg Ala Ser Phe Ser Ser
            180                 185                 190

Val Gly Ala Glu Leu Glu Val Met Ala Pro Gly Ala Gly Val Tyr Ser
        195                 200                 205

Thr Tyr Pro Thr Ser Thr Tyr Ala Thr Leu Asn Gly Thr Ser Met Ala
    210                 215                 220

Ser Pro His Val Ala Gly Ala Ala Ala Leu Ile Leu Ser Lys His Pro
225                 230                 235                 240

Asn Leu Ser Ala Ser Gln Val Arg Asn Arg Leu Ser Ser Thr Ala Thr
                245                 250                 255

Tyr Leu Gly Ser Ser Phe Tyr Tyr Gly Lys Gly Leu Ile Asn Val Glu
            260                 265                 270

Ala Ala Ala Gln
        275

<210> SEQ ID NO 56
<211> LENGTH: 271
<212> TYPE: PRT
<213> ORGANISM: Artificial Sequence
<220> FEATURE:
<223> OTHER INFORMATION: Synthetic
<220> FEATURE:
```

```
<221> NAME/KEY: Misc_feature
<222> LOCATION: (101)..(101)
<223> OTHER INFORMATION: Xaa denotes any amino acid

<400> SEQUENCE: 56

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Ala Tyr Ala Val Lys Val Leu Gly
                85                  90                  95

Ala Ser Gly Ser Xaa Gly Ser Val Ser Ser Ile Ala Gln Gly Leu Glu
            100                 105                 110

Trp Ala Gly Asn Asn Gly Met His Val Ala Asn Leu Ser Leu Gly Ser
            115                 120                 125

Pro Ser Pro Ser Ala Thr Leu Glu Gln Ala Val Asn Ser Ala Thr Ser
130                 135                 140

Arg Gly Val Leu Val Val Ala Ala Ser Gly Asn Ser Gly Ala Gly Ser
145                 150                 155                 160

Ile Ser Tyr Pro Ala Arg Tyr Ala Asn Ala Met Ala Val Gly Ala Thr
                165                 170                 175

Asp Gln Asn Asn Asn Arg Ala Ser Phe Ser Gln Tyr Gly Ala Gly Leu
            180                 185                 190

Asp Ile Val Ala Pro Gly Val Asn Val Gln Ser Thr Tyr Pro Gly Ser
        195                 200                 205

Thr Tyr Ala Ser Leu Asn Gly Thr Ser Met Ala Thr Pro His Val Ala
    210                 215                 220

Gly Ala Ala Ala Leu Val Lys Gln Lys Asn Pro Ser Trp Ser Asn Val
225                 230                 235                 240

Gln Ile Arg Asn His Leu Lys Asn Thr Ala Thr Ser Leu Gly Ser Thr
                245                 250                 255

Asn Leu Tyr Gly Ser Gly Leu Val Asn Ala Glu Ala Ala Thr Arg
            260                 265                 270

<210> SEQ ID NO 57
<211> LENGTH: 276
<212> TYPE: PRT
<213> ORGANISM: Artificial Sequence
<220> FEATURE:
<223> OTHER INFORMATION: Synthetic
<220> FEATURE:
<221> NAME/KEY: Misc_feature
<222> LOCATION: (103)..(103)
<223> OTHER INFORMATION: Xaa denotes any amino acid

<400> SEQUENCE: 57

Ala Gln Thr Val Pro Tyr Gly Ile Pro Leu Ile Lys Ala Asp Lys Val
1               5                   10                  15

Gln Ala Gln Gly Phe Lys Gly Ala Asn Val Lys Val Ala Val Leu Asp
            20                  25                  30

Thr Gly Ile Gln Ala Ser His Pro Asp Leu Asn Val Val Gly Gly Ala
        35                  40                  45
```

```
Ser Phe Val Ala Gly Glu Ala Tyr Asn Thr Asp Gly Asn Gly His Gly
     50                  55                  60

Thr His Val Ala Gly Thr Val Ala Ala Leu Asp Asn Thr Thr Gly Val
 65                  70                  75                  80

Leu Gly Val Ala Pro Ser Val Ser Leu Ala Tyr Ala Val Lys Val Leu
                 85                  90                  95

Asn Ser Ser Gly Ser Gly Xaa Thr Tyr Ser Gly Ile Val Ser Gly Ile
            100                 105                 110

Glu Trp Ala Thr Thr Asn Gly Met Asp Val Ile Asn Met Ser Leu Gly
            115                 120                 125

Gly Pro Ser Gly Ser Thr Ala Met Lys Gln Ala Val Asp Asn Ala Tyr
        130                 135                 140

Ala Arg Gly Val Val Val Ala Ala Gly Asn Ser Gly Ser Ser
145                 150                 155                 160

Gly Asn Thr Asn Thr Ile Gly Tyr Pro Ala Lys Tyr Asp Ser Val Ile
                165                 170                 175

Ala Val Gly Ala Val Asp Ser Asn Ser Asn Arg Ala Ser Phe Ser Ser
            180                 185                 190

Val Gly Ala Glu Leu Glu Val Met Ala Pro Gly Ala Gly Val Tyr Ser
        195                 200                 205

Thr Tyr Pro Thr Ser Thr Tyr Ala Thr Leu Asn Gly Thr Ser Met Ala
    210                 215                 220

Ser Pro His Val Ala Gly Ala Ala Ala Leu Ile Leu Ser Lys His Pro
225                 230                 235                 240

Asn Leu Ser Ala Ser Gln Val Arg Asn Arg Leu Ser Ser Thr Ala Thr
                245                 250                 255

Tyr Leu Gly Ser Ser Phe Tyr Tyr Gly Lys Gly Leu Ile Asn Val Glu
            260                 265                 270

Ala Ala Ala Gln
        275

<210> SEQ ID NO 58
<211> LENGTH: 271
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (102)..(102)
<223> OTHER INFORMATION: Xaa denotes any amino acid

<400> SEQUENCE: 58

Ala Gln Ser Val Pro Trp Gly Ile Ser Arg Val Gln Ala Pro Ala Ala
 1               5                  10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
 65                  70                  75                  80

Gly Val Ala Pro Ser Ala Glu Leu Ala Tyr Ala Val Lys Val Leu Gly
                 85                  90                  95

Ala Ser Gly Ser Gly Xaa Ser Val Ser Ser Ile Ala Gln Gly Leu Glu
```

```
              100                 105                 110
Trp Ala Gly Asn Asn Gly Met His Val Ala Asn Leu Ser Leu Gly Ser
            115                 120                 125

Pro Ser Pro Ser Ala Thr Leu Glu Gln Ala Val Asn Ser Ala Thr Ser
130                 135                 140

Arg Gly Val Leu Val Ala Ala Ser Gly Asn Ser Gly Ala Gly Ser
145                 150                 155                 160

Ile Ser Tyr Pro Ala Arg Tyr Ala Asn Ala Met Ala Val Gly Ala Thr
                165                 170                 175

Asp Gln Asn Asn Arg Ala Ser Phe Ser Gln Tyr Gly Ala Gly Leu
            180                 185                 190

Asp Ile Val Ala Pro Gly Val Asn Val Gln Ser Thr Tyr Pro Gly Ser
            195                 200                 205

Thr Tyr Ala Ser Leu Asn Gly Thr Ser Met Ala Thr Pro His Val Ala
            210                 215                 220

Gly Ala Ala Ala Leu Val Lys Gln Lys Asn Pro Ser Trp Ser Asn Val
225                 230                 235                 240

Gln Ile Arg Asn His Leu Lys Asn Thr Ala Thr Ser Leu Gly Ser Thr
                245                 250                 255

Asn Leu Tyr Gly Ser Gly Leu Val Asn Ala Glu Ala Ala Thr Arg
            260                 265                 270

<210> SEQ ID NO 59
<211> LENGTH: 276
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa denotes any amino acid

<400> SEQUENCE: 59

Ala Gln Thr Val Pro Tyr Gly Ile Pro Leu Ile Lys Ala Asp Lys Val
1               5                   10                  15

Gln Ala Gln Gly Phe Lys Gly Ala Asn Val Lys Val Ala Val Leu Asp
            20                  25                  30

Thr Gly Ile Gln Ala Ser His Pro Asp Leu Asn Val Val Gly Gly Ala
        35                  40                  45

Ser Phe Val Ala Gly Glu Ala Tyr Asn Thr Asp Gly Asn Gly His Gly
    50                  55                  60

Thr His Val Ala Gly Thr Val Ala Ala Leu Asp Asn Thr Thr Gly Val
65                  70                  75                  80

Leu Gly Val Ala Pro Ser Val Ser Leu Ala Tyr Ala Val Lys Val Leu
                85                  90                  95

Asn Ser Ser Gly Ser Gly Thr Xaa Tyr Ser Gly Ile Val Ser Gly Ile
            100                 105                 110

Glu Trp Ala Thr Thr Asn Gly Met Asp Val Ile Asn Met Ser Leu Gly
        115                 120                 125

Gly Pro Ser Gly Ser Thr Ala Met Lys Gln Ala Val Asp Asn Ala Tyr
    130                 135                 140

Ala Arg Gly Val Val Val Val Ala Ala Gly Asn Ser Gly Ser Ser
145                 150                 155                 160

Gly Asn Thr Asn Thr Ile Gly Tyr Pro Ala Lys Tyr Asp Ser Val Ile
                165                 170                 175
```

```
Ala Val Gly Ala Val Asp Ser Asn Ser Asn Arg Ala Ser Phe Ser Ser
            180                 185                 190

Val Gly Ala Glu Leu Glu Val Met Ala Pro Gly Ala Gly Val Tyr Ser
        195                 200                 205

Thr Tyr Pro Thr Ser Thr Tyr Ala Thr Leu Asn Gly Thr Ser Met Ala
    210                 215                 220

Ser Pro His Val Ala Gly Ala Ala Leu Ile Leu Ser Lys His Pro
225                 230                 235                 240

Asn Leu Ser Ala Ser Gln Val Arg Asn Arg Leu Ser Ser Thr Ala Thr
                245                 250                 255

Tyr Leu Gly Ser Ser Phe Tyr Tyr Gly Lys Gly Leu Ile Asn Val Glu
            260                 265                 270

Ala Ala Ala Gln
        275

<210> SEQ ID NO 60
<211> LENGTH: 271
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (103)..(103)
<223> OTHER INFORMATION: Xaa denotes any amino acid

<400> SEQUENCE: 60

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Ala Tyr Ala Val Lys Val Leu Gly
                85                  90                  95

Ala Ser Gly Ser Gly Ser Xaa Val Ser Ser Ile Ala Gln Gly Leu Glu
            100                 105                 110

Trp Ala Gly Asn Asn Gly Met His Val Ala Asn Leu Ser Leu Gly Ser
        115                 120                 125

Pro Ser Pro Ser Ala Thr Leu Glu Gln Ala Val Asn Ser Ala Thr Ser
    130                 135                 140

Arg Gly Val Leu Val Val Ala Ala Ser Gly Asn Ser Gly Ala Gly Ser
145                 150                 155                 160

Ile Ser Tyr Pro Ala Arg Tyr Ala Asn Ala Met Ala Val Gly Ala Thr
                165                 170                 175

Asp Gln Asn Asn Asn Arg Ala Ser Phe Ser Gln Tyr Gly Ala Gly Leu
            180                 185                 190

Asp Ile Val Ala Pro Gly Val Asn Val Gln Ser Thr Tyr Pro Gly Ser
        195                 200                 205

Thr Tyr Ala Ser Leu Asn Gly Thr Ser Met Ala Thr Pro His Val Ala
    210                 215                 220

Gly Ala Ala Ala Leu Val Lys Gln Lys Asn Pro Ser Trp Ser Asn Val
225                 230                 235                 240
```

Gln Ile Arg Asn His Leu Lys Asn Thr Ala Thr Ser Leu Gly Ser Thr
                245                 250                 255

Asn Leu Tyr Gly Ser Gly Leu Val Asn Ala Glu Ala Thr Arg
            260                 265                 270

<210> SEQ ID NO 61
<211> LENGTH: 5
<212> TYPE: PRT
<213> ORGANISM: Artificial Sequence
<220> FEATURE:
<223> OTHER INFORMATION: Synthetic

<400> SEQUENCE: 61

Gly Gly Ala Ser Gly
1               5

<210> SEQ ID NO 62
<211> LENGTH: 6
<212> TYPE: PRT
<213> ORGANISM: Artificial Sequence
<220> FEATURE:
<223> OTHER INFORMATION: Synthetic

<400> SEQUENCE: 62

Ala Ala Gly Gly Gly Gly
1               5

<210> SEQ ID NO 63
<211> LENGTH: 6
<212> TYPE: PRT
<213> ORGANISM: Artificial Sequence
<220> FEATURE:
<223> OTHER INFORMATION: Synthetic

<400> SEQUENCE: 63

Ala Ala Gly Gly Gly Ser
1               5

<210> SEQ ID NO 64
<211> LENGTH: 6
<212> TYPE: PRT
<213> ORGANISM: Artificial Sequence
<220> FEATURE:
<223> OTHER INFORMATION: Synthetic

<400> SEQUENCE: 64

Ala Ala Gly Ser Gly Gly
1               5

<210> SEQ ID NO 65
<211> LENGTH: 6
<212> TYPE: PRT
<213> ORGANISM: Artificial Sequence
<220> FEATURE:
<223> OTHER INFORMATION: Synthetic

<400> SEQUENCE: 65

Ala Ala Ser Gly Ser Gly
1               5

<210> SEQ ID NO 66
<211> LENGTH: 6
<212> TYPE: PRT
<213> ORGANISM: Artificial Sequence
<220> FEATURE:
<223> OTHER INFORMATION: Synthetic

```
<400> SEQUENCE: 66

Ala Ala Ser Gly Thr Gly
1               5

<210> SEQ ID NO 67
<211> LENGTH: 6
<212> TYPE: PRT
<213> ORGANISM: Artificial Sequence
<220> FEATURE:
<223> OTHER INFORMATION: Synthetic

<400> SEQUENCE: 67

Ala Ala Thr Gly Ser Gly
1               5

<210> SEQ ID NO 68
<211> LENGTH: 6
<212> TYPE: PRT
<213> ORGANISM: Artificial Sequence
<220> FEATURE:
<223> OTHER INFORMATION: Synthetic

<400> SEQUENCE: 68

Ala Ala Thr Gly Thr Gly
1               5

<210> SEQ ID NO 69
<211> LENGTH: 5
<212> TYPE: PRT
<213> ORGANISM: Artificial Sequence
<220> FEATURE:
<223> OTHER INFORMATION: Synthetic

<400> SEQUENCE: 69

Ser Ser Gly Ala Ala
1               5
```